United States Patent
Skahan et al.

(10) Patent No.: US 8,070,703 B2
(45) Date of Patent: Dec. 6, 2011

(54) ELECTRICALLY STIMULATING ORTHOTIC DEVICE AND SEGMENTED LINER

(75) Inventors: Michael Skahan, Vista, CA (US); Kevin Lunau, Valley Center, CA (US); Timothy Stoltenburg, Vista, CA (US); Robert Gilmour, Auckland (NZ)

(73) Assignee: Vision Quest Industries Incorporated, Irvine, CA (US)

( * ) Notice: Subject to any disclaimer, the term of this patent is extended or adjusted under 35 U.S.C. 154(b) by 0 days.

(21) Appl. No.: 12/468,794

(22) Filed: May 19, 2009

(65) Prior Publication Data
US 2009/0287126 A1 Nov. 19, 2009

(51) Int. Cl.
*A61F 5/00* (2006.01)
(52) U.S. Cl. .......................................... 602/23; 602/26
(58) Field of Classification Search .............. 602/16, 602/20–22, 23–27; 128/882
See application file for complete search history.

(56) References Cited

U.S. PATENT DOCUMENTS

| | | | |
|---|---|---|---|
| 3,911,910 A | 10/1975 | Oesau | |
| 4,467,809 A | 8/1984 | Brighton | |
| 4,487,834 A | 12/1984 | Brighton | |
| 4,586,495 A * | 5/1986 | Petrofsky | 602/2 |
| 4,759,368 A | 7/1988 | Spanton | |
| 4,796,631 A * | 1/1989 | Grigoryev | 607/49 |
| 4,872,448 A | 10/1989 | Johnson et al. | |
| 4,917,092 A | 4/1990 | Todd | |
| 4,938,207 A | 7/1990 | Vargo et al. | |
| 5,014,699 A | 5/1991 | Pollack | |
| 5,230,697 A | 7/1993 | Castillo et al. | |
| 5,273,033 A | 12/1993 | Hoffman | |
| 5,277,698 A | 1/1994 | Taylor | |
| 5,288,287 A | 2/1994 | Castillo et al. | |
| 5,316,547 A | 5/1994 | Gildersleeve | |
| 5,542,911 A | 8/1996 | Cassford et al. | |
| 5,628,722 A * | 5/1997 | Solomonow et al. | 602/26 |
| 5,645,524 A | 7/1997 | Doyle | |
| 6,064,912 A * | 5/2000 | Kenney | 607/48 |
| 6,110,135 A | 8/2000 | Madow et al. | |
| 6,456,884 B1 | 9/2002 | Kenney | |
| 7,022,506 B2 | 4/2006 | Brighton | |
| 7,130,692 B2 | 10/2006 | Brighton | |
| 7,158,835 B2 | 1/2007 | Brighton | |
| 7,167,753 B2 | 1/2007 | Brighton | |

(Continued)

FOREIGN PATENT DOCUMENTS

DE 20116887 2/2002

(Continued)

OTHER PUBLICATIONS

Zizic TM, The treatment of osteoarthritis of the knee with pulsed electrical stimulation. J Rheumatol. 1995;22:1757-1761.

(Continued)

*Primary Examiner* — Michael A. Brown

(57) ABSTRACT

According to various embodiments of the invention, an orthotic device comprises an upper support member adapted to be secured to a thigh; a lower support member adapted to be secured to a lower leg; a means of connecting the upper support member to the lower support member; a conformable, discrete liner segment attached to the upper or lower support member configured to provide a conforming interface with the thigh or lower leg; a first electrode disposed on the liner segment configured to contact the leg; a second electrode configured to contact the leg; and an electrostimulation unit in electrical contact with the first and second electrodes and configured to provide an electrophysical modality to the leg.

22 Claims, 18 Drawing Sheets

U.S. PATENT DOCUMENTS

| | | | |
|---|---|---|---|
| 7,215,995 | B2 | 5/2007 | Brighton |
| 7,354,748 | B2 | 4/2008 | Brighton |
| 7,465,546 | B2 | 12/2008 | Brighton |
| 7,468,264 | B2 | 12/2008 | Brighton |
| 2002/0165590 | A1 | 11/2002 | Crowe |
| 2002/0188229 | A1 | 12/2002 | Ryaby |
| 2003/0153848 | A1 | 8/2003 | Talish |
| 2003/0187375 | A1 | 10/2003 | Gaylord |
| 2004/0015208 | A1 | 1/2004 | Haugland |
| 2004/0267333 | A1 | 12/2004 | Kronberg |
| 2006/0135896 | A1 | 6/2006 | Latimer |
| 2006/0190043 | A1 | 8/2006 | Brighton |
| 2006/0293724 | A1 | 12/2006 | Kronberg |
| 2007/0038252 | A1 | 2/2007 | Carroll |
| 2007/0112394 | A1 | 5/2007 | Nathan |
| 2007/0191912 | A1 | 8/2007 | Fischer |
| 2007/0299472 | A1 | 12/2007 | Brighton |
| 2008/0281392 | A1 | 11/2008 | Paolizzi |
| 2009/0287126 | A1 | 11/2009 | Skahan |

FOREIGN PATENT DOCUMENTS

| | | |
|---|---|---|
| WO | 2005/087148 | 9/2005 |

OTHER PUBLICATIONS

Electrical Stimulation helps delay knee replacement surgery. Mont MA, Hungerford DS, Caldwell JR, Hoffman KC, Zizic TM. BioMechanics vol. CII, No. 5, May 2005.

Osteoarthritis and Cartilage; D. Garland, et al.; vol. 15, Issue 6, Jun. 2007, pp. 630-637.

International Search Report for International Application No. PCT/US2005/008010 (4 Pages) (dated May 7, 2005).

Pulsed Electrical Stimulation to Defer TKA in Patients With Knee Osteoarthritis from Orthopedics Oct. 1, 2006; by M.A. Mont, et al., published in http://www.orthosupersite.com/view.aspx?rid=18717—printed on May 18, 2010.

Farr, Jack, et al., Pulsed Electrical Stimulation in Patients With Osteoarthritis of the Knee: Follow Up in 288 Patients Who Had Failed Non-Operative Therapy, 2006, pp. 227-233, Orthopaedic Surgery, Surgical Technology International XV, Universal Medical Press, Inc., San Francisco, CA.

O'Driscoll SW., et al., Durability of regenerated articular cartilage produced by free autogenous periosteal grafts in major full-thickness defects in joint surfaces under the influence of continuous passive motion. A follow-up report at one year. J Bone Joint Surg Am. Apr. 1988;70(4):595-606.

O'Driscoll SW, et al., The chondrogenic potential of free autogenous periosteal grafts for biological resurfacing of major full-thickness defects in joint surfaces under the influence of continuous passive motion. An experimental investigation in the rabbit. J Bone Joint Surg Am. Sep. 1986;68(7):1017-1035.

O'Driscoll SW, et al., The repair of major osteochondral defects in joint surfaces by neochondrogenesis with autogenous osteoperiosteal grafts stimulated by continuous passive motion. An experimental investigation in the rabbit. Clin Orthop Relat Res. Jul. 1986;(208):131-140.

O'Driscoll SW, et al., A method for quantitative analysis of ratios of types I and II collagen in small samples of articular cartilage. Anal Biochem. Mar. 1985;145(2):277-285.

O'Driscoll SW, et al., The induction of neochondrogenesis in free intra-articular periosteal autografts under the influence of continuous passive motion. An experimental investigation in the rabbit. J Bone Joint Surg Am. Oct. 1984;66(8):1248-1257.

Salter RB. The physiologic basis of continuous passive motion for articular cartilage healing and regeneration. Hand Clin. May 1994;10(2):211-219.

Salter RB, et al., The protective effect of continuous passive motion on living articular cartilage in acute septic arthritis: an experimental investigation in the rabbit. Clin Orthop Relat Res. Sep. 1981;(159):223-247.

Salter RB, et al., The biological effect of continuous passive motion on the healing of full-thickness defects in articular cartilage. An experimental investigation in the rabbit. J Bone Joint Surg Am. Dec. 1980;62(8):1232-1251.

PCT International Search Report and Written Opinion (PCT/US2005/008010) dated Jun. 22, 2005 (11 pages).

PCT Notification of Transmittal of the International Preliminary Report on Patentability (PCT/US2005/008010) dated Jun. 12, 2006 (6 pages).

PCT Written Opinion of the International Preliminary Examining Authority (PCT/US2005/008010) dated Mar. 27, 2006 (7 pages).

* cited by examiner

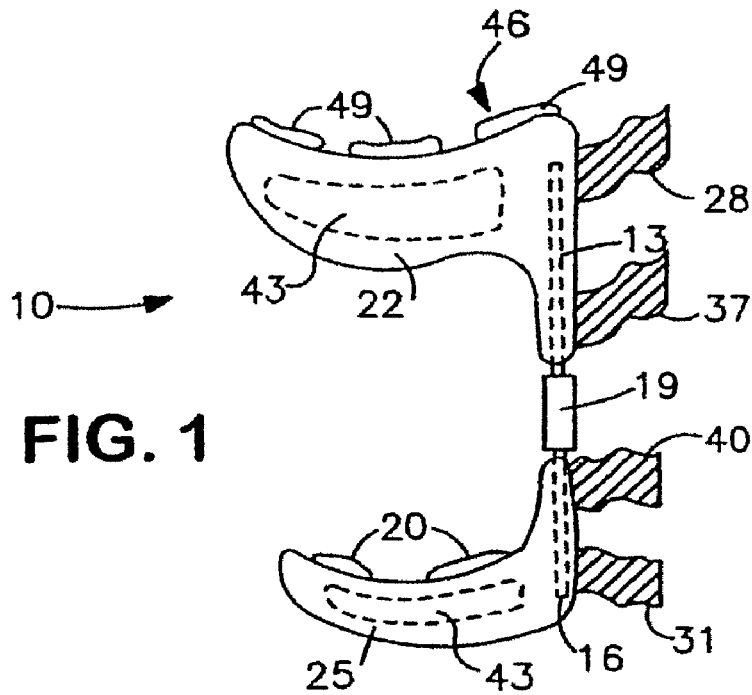
FIG. 1
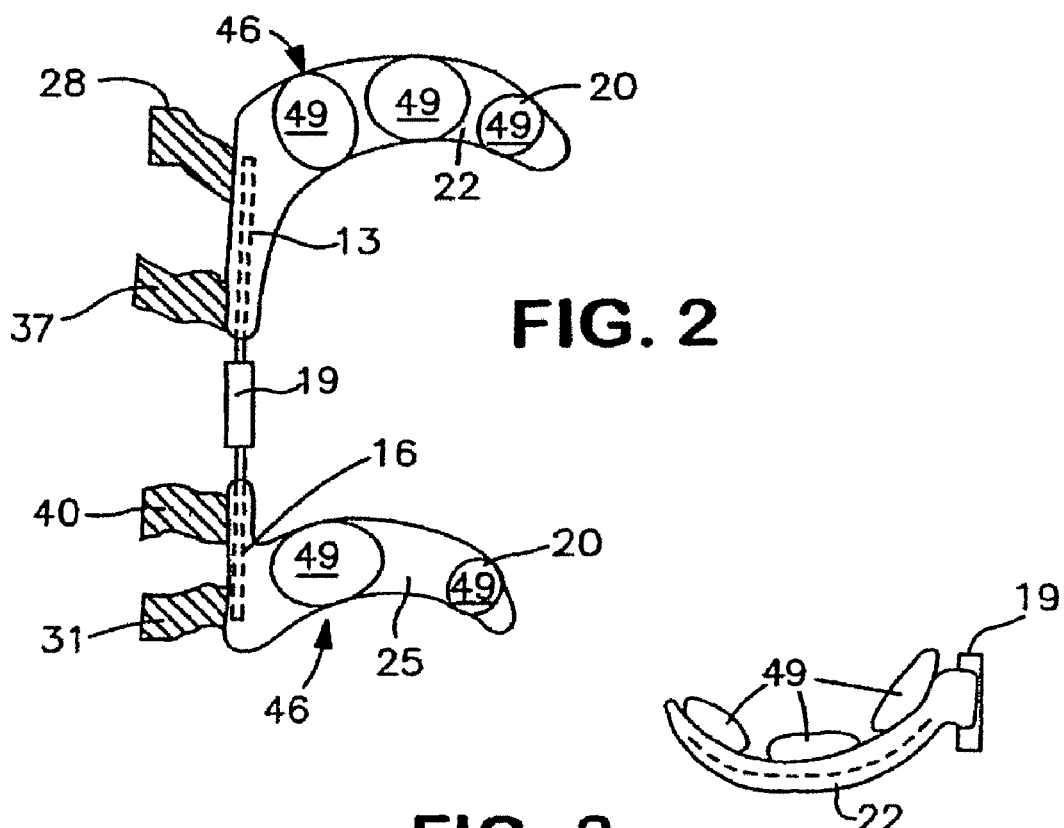
FIG. 2
FIG. 3

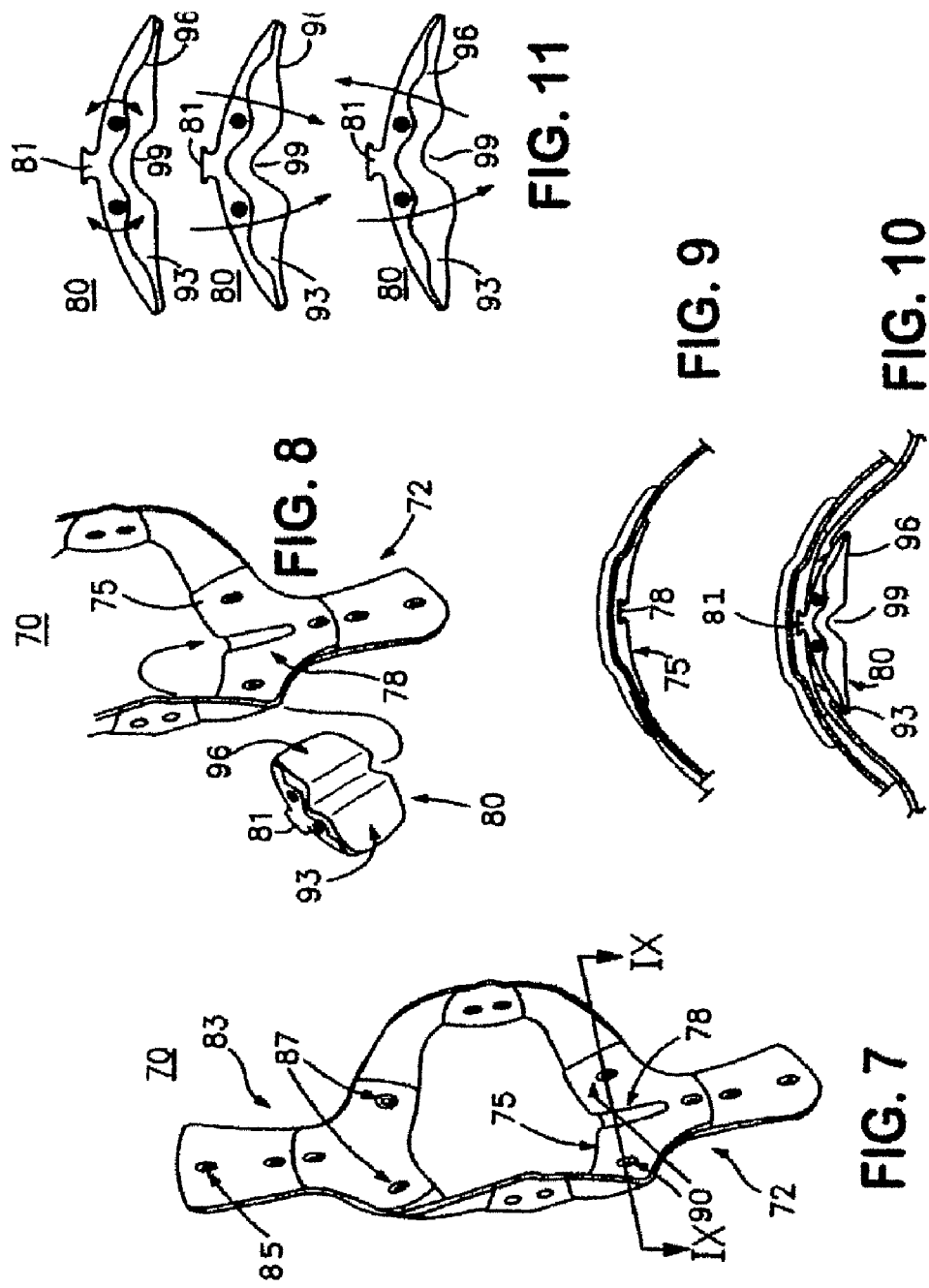

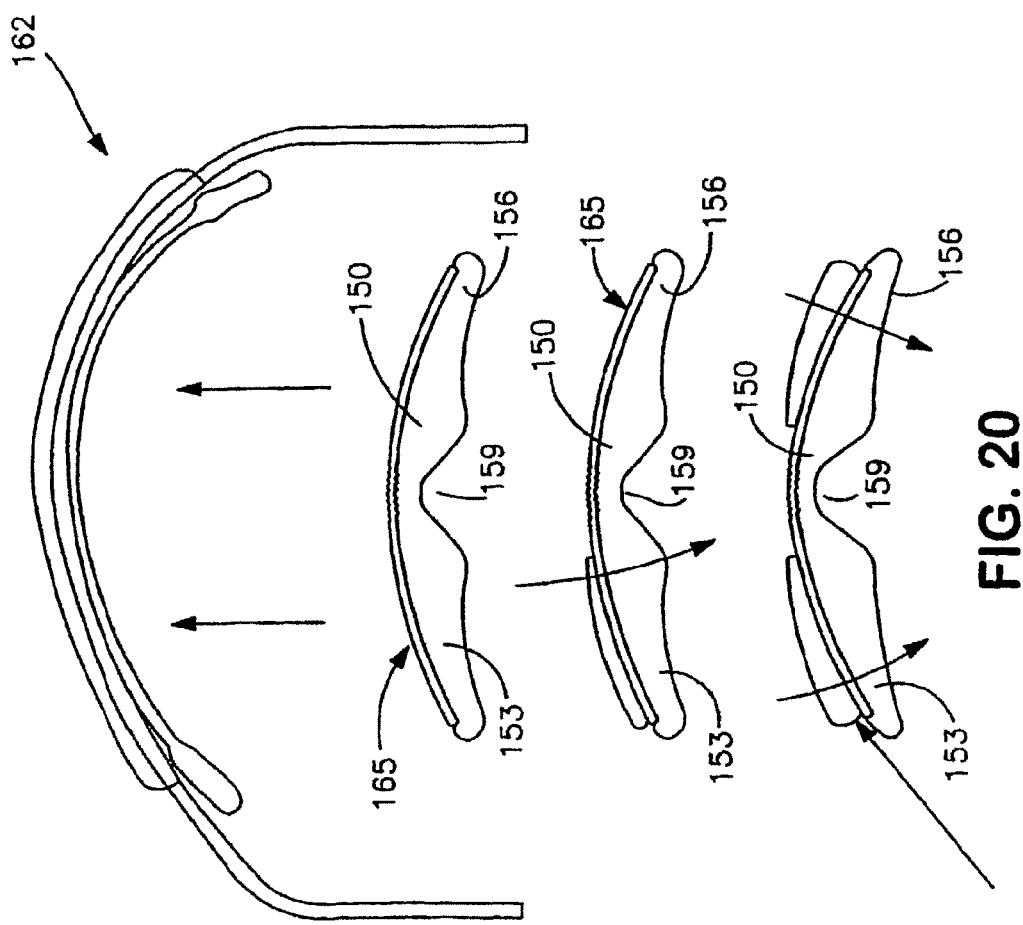
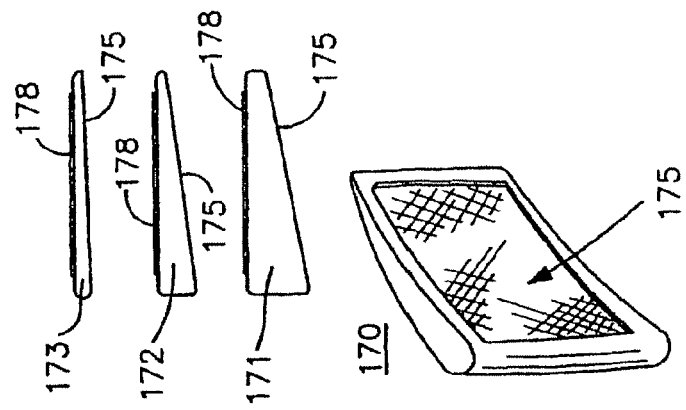

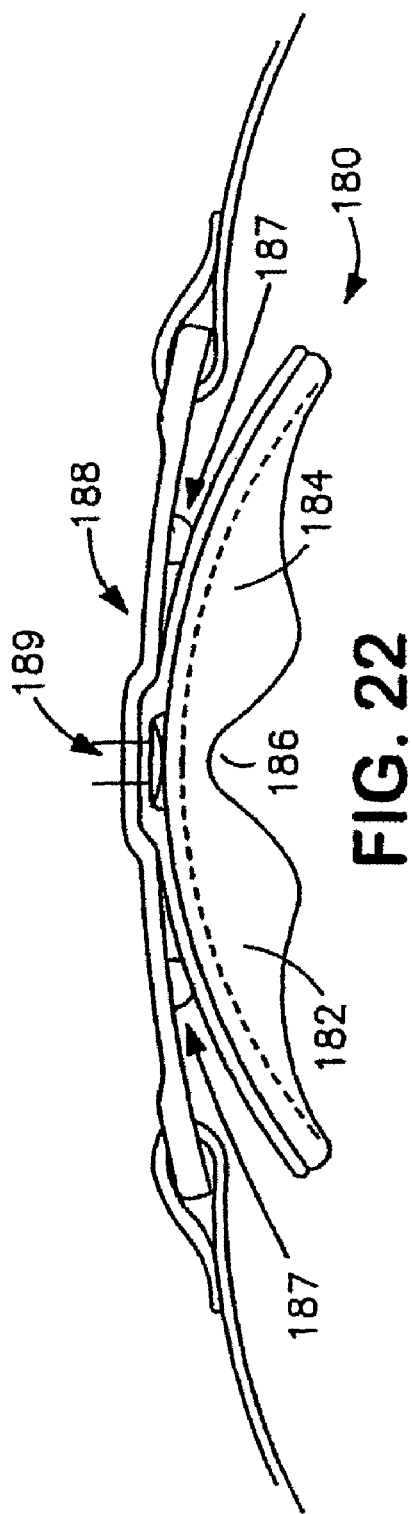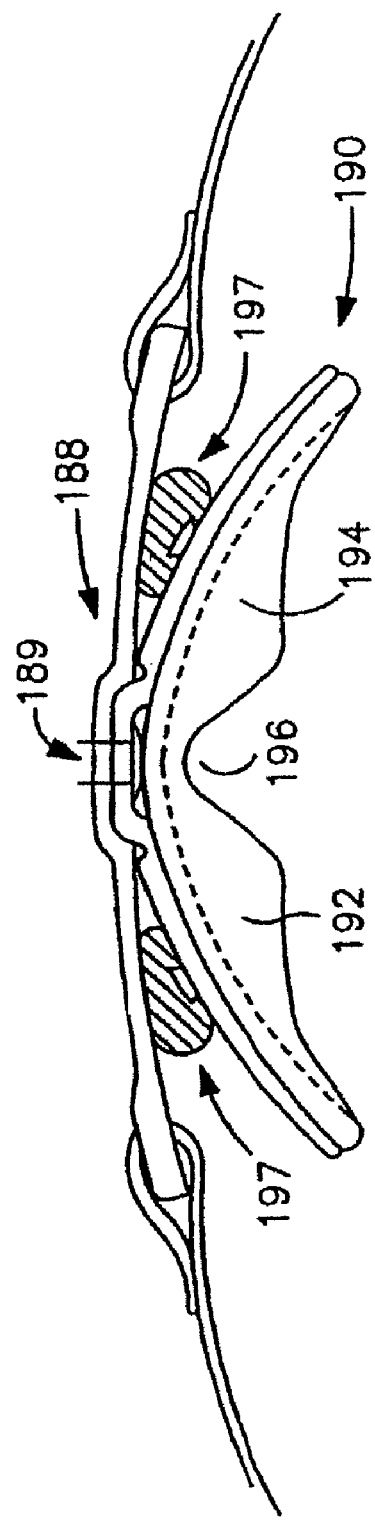

ELECTRICALLY STIMULATING ORTHOTIC DEVICE AND SEGMENTED LINER

CROSS-REFERENCE TO RELATED APPLICATIONS

This application claims priority from U.S. application Ser. No. 10/591,966 filed Sep. 7, 2006, now U.S. Pat. No. 7,758,527, which claims priority from PCT Application Serial Number PCT/US05/08010 filed Mar. 10, 2005, which claims priority from New Zealand Application Serial Number NZ531705 filed Mar. 10, 2004, each of which is hereby incorporated herein by reference in its entirety.

TECHNICAL FIELD

The present invention relates generally to orthotic devices, and more particularly, some embodiments relate to knee braces adapted to provide electrostimulation and to conform to a wearer's leg.

DESCRIPTION OF THE RELATED ART

Orthotic devices generally include a substantially rigid biomechanical element that forms the basis of the skeletal support that is required for the majority of these devices, which include braces, supports and splints.

The human knee generally comprises an articulated joint between the thigh and the calf muscles that supports the weight of the human body while the person is standing, walking or running. The knee joint is primarily held together by four ligaments; namely, the anterior and posterior cruciate ligaments and the medial and lateral collateral ligaments. The knee joint can be overly weakened by injuries arising out of cartilage damage and ligament strain, which may be caused, by sports injuries, as well as from everyday exercising, or physiological problems such as osteoarthritis. Thus, the human knee is subjected to a variety of stresses and strains particularly during running and jumping movements. Athletes, in particular, are apt to incur a knee injury as a result of a blow to the knee or to a twisting of the knee, which can commonly occur in various contact sports or high stress sports, such as skiing.

There are a variety of knee braces available on the market or through healthcare providers. These range from braces that tend to totally immobilize the knee to flexible elastic bandages that are intended to provide some flexibility while eliminating lateral movement of the ligaments that support the knee. Some of these are intended to be worn as a relatively permanent device for long-term wear or braces that are intended to be worn for a short period of time during overly strenuous for a short period of time for a weakened knee. The braces have as their primary object to allow for pivoting the knee while preventing any unnatural movement that may aggravate the knee ligaments. Some braces are meant to provide a constant or variable "unloading" force on the knee joint to alleviate pain, such as pain caused by Osteoarthritis. While the braces are intended to allow for a natural movement of the knee joint while a person undergoes walking, running, jumping, skating, various other athletic activities, they are also intended to prevent sudden movement of the upper and lower legs to one side or the other and to prevent twisting or rotation of the lower leg relative to the upper leg about the vertical axis, and/or to provide a pain-relieving force to the joint.

Typically, the knee braces are held in place by flexible straps, which wrap about the user's thigh and calf above and below the knee, respectively. In this manner, the rigid hinge of the knee brace remains positioned on either side of the user's knee so as to mimic the hinged joint of the knee. However, it is not uncommon for the user's bodily motions to cause the flexible straps to move relative to the person's leg, thereby misaligning the knee brace with respect to the knee. This movement of the brace straps with respect to the user not only cause misalignment and therefore misapplication of the orthotic device, but also cause irritation of the user's skin by this unintended rubbing.

Orthotic devices must engage effectively with soft tissue in order to provide the desired support. In many parts of the body the soft tissue will move, for example by expanding or contracting as result of muscle movement. As a soft tissue changes shape, parts of the skin lose contact with the liner of the orthotic device. This reduced contact with the liner can cause the orthotic device to lose position, or move relative to the user and therefore become ineffective. Typical devices provide measures for tightening the brace to maintain contact. This causes discomfort, prevents the skin from breathing, and can irritate the skin about the edges of the device and the liner.

The objective of any rigid knee brace is to exert a predictable force on the user's underlying skeleton. In particular, the objective is to exert a force on the tibia with respect to the femur in the user's body mass above the knee. By definition, knee braces are applied to soft tissue lying between the brace and the user's skeleton. The rigid element may include some form of liner that contacts the body of the user. The liner may have an outer fabric that is designed to contact the user's skin directly or, alternatively, to engage with clothing that a user may be wearing about the pat of the anatomy to which the orthotic device is to be attached. Soft tissue is mobile and moves in a cycle corresponding to a user's gait, whether it be through running, walking or other physical movement common to the human knee. The most mobile soft tissue is the quadriceps mechanism lying in front of the femur in the anterior thigh region. The central reference point for a knee brace is the knee joint line. In construction, an orthotic device such as a knee brace would use a joint mechanism, which mimics the movement of the joint to be supported, such as the knee, which is not just a simple hinge. Since each user's body shape is unique, the interface between the orthotic device and the user's leg cannot be predetermined in the manufacture of such a device.

Degenerative joint disease, osteoarthritis, and other joint diseases or injuries may be treated through various methods of electrical stimulation. Surface electrical stimulation (SES) treats these conditions using sub-sensory electrical pulses. Other methods of electrostimulation include Neuromuscular Electrical Stimulation, Interferential Stimulation, High Volt Galvanic Stimulation, Electromagnetic and Pulsed Electromagnetic Field Stimulation, Transcutaneous Electrical Nerve Stimulation, and Micro Current Electrical Stimulation.

BRIEF SUMMARY OF EMBODIMENTS OF THE INVENTION

According to various embodiments of the invention, an orthotic device comprises an upper support member adapted to be secured to a thigh; a lower support member adapted to be secured to a lower leg, said support members being rigid, semi-rigid, compressive (i.e. a sleeve/wrap), or a combination of the above; a means of connecting the upper support member to the lower support member; a conformable, discrete liner segment attached to the upper or lower support member configured to provide a conforming interface with the thigh or lower leg; a first electrode disposed on the liner segment configured to contact the leg; a second electrode configured to contact the leg; and an electrostimulation unit in electrical contact with the first and second electrodes and configured to provide an electrophysical modality to the leg.

According to an embodiment of the invention, an orthotic liner comprises a first surface attachable to a support member of an orthotic device; a conductive volume configured to conform to a part of an anatomy; and a second surface configured to interface with the part of the anatomy; wherein the conductive volume and second surface are configured to transmit electrostimulation signals to the part of the anatomy.

According to another embodiment of the invention, an electrostimulation unit comprises an electrostimulation signal generator configured to be attached to a support member of an orthotic brace and configured to provide an electrophysical modality to a circuit comprising a plurality of electrodes and a portion of an anatomy; wherein an electrode is disposed on a conformable, discrete liner attachable to a support member of the orthotic brace.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 1 is a front elevation of a knee brace according to the present invention;

FIG. 2 is a rear elevation of the brace of FIG. 1;

FIG. 3 is a partial plan view of the brace of FIG. 1;

FIG. 7 is a perspective view of an orthotic device adapted for receiving a segmented tibial liner element;

FIG. 8 is a view partially in section of the orthotic device in FIG. 7 illustrating attachment of the segment and tibial liner element;

FIG. 9 is a cross section view taken through line IX-IX in FIG. 7;

FIG. 10 is a cross section view similar to FIG. 9 and also illustrating attachment of the segmented tibial liner;

FIG. 11 illustrates a preferred embodiment of a segmented active tibial management liner;

FIG. 20 is a cross sectional view of an orthotic device similar to the orthotic device shown in FIG. 7 illustrating a further embodiment of a segmented tibial liner;

FIG. 21 illustrates an embodiment of a chock for use with the segmented tibial liner in FIG. 20;

FIG. 22 is a cross section view showing a segmented tibial liner receptacle plate in and alternative manner of attaching a segmented tibial liner; and FIG. 23 is a cross section view similar to FIG. 22, showing a still further embodiment of a manner of attaching a segmented tibial liner.

Figure 4A:
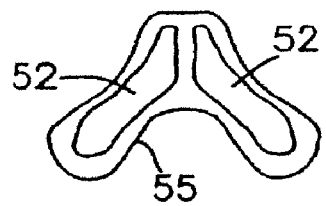
FIG. 4, consisting of FIGS. 4A and 4B, is a plan view and side elevation, respectively, of a liner element of the present invention.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

Referring now to the drawings in detail, wherein like reference characters refer to like elements, there is shown in FIG. 1 a knee brace 10 according the present invention. The invention will be described with reference to a knee brace; however, it will be understood that the invention is also applicable to other orthotic devices such as an ankle, back, arm, shoulder, or wrist brace, and other devices for relieving pain in any body portion of the user. Although this invention will be described by way of example and with reference to preferred embodiments thereof, it is to be understood that modifications or improvements may be made thereto without departing from the scope or spirit of the invention. It should be noted that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be included within the present invention.

Referring to FIG. 1, a knee brace 10 is shown having a biomechanical support comprising two substantially rigid arms, 13 and 16, which are joined together by a hinge assembly 19. Connected to the rigid arms are upper and lower structures 22 and 25, respectively which, together with straps 28 and 31 are used to form a primary engagement with the user's leg above and below the knee 34. This engagement can be augmented by further straps 37 and 40. The hinge assembly 19 has a predetermined range of movement corresponding to the desired range of flexion/extension of the knee of the user. The upper and lower support structures 22, 25 are generally referred to as cuffs.

The upper cuff 22 is adapted to be secured to the user's thigh (femur) and the lower cuff 25 is adapted to be secured to the lower leg or calf (tibia). In this way the hinge assembly 19 is placed adjacent the axis of the user's knee joint, thereby allowing the knee brace 10 to substantially mimic the bending of the user's knee as the user goes about his or her otherwise normal activities. In the preferred embodiments, upper and lower cuffs 22, 25 comprise adaptive support structures that are constructed from a semi-rigid material such as a thermoplastic elastomer or a thermoplastic rubber.

Furthermore, the preferred embodiments may include a rigid material 43 that is integrally moulded into upper and lower structures 22, 25, or is alternatively fixedly attached to the strictures. Rigid material 43 has a greater rigidity than the semi-rigid material from which upper and lower structures 22, 25 are moulded, and is preferably malleable. In the preferred embodiments, rigid material 43 comprises a sheet aluminum material which has an appropriate thickness (for example, on the order of about 1-2 two millimetres thick), or other deformable metal, so that it may be easily shaped by the user using his or her hands to assist the adaptive material from which the structures 22, 25 are manufactured to generally conform to the portion of the anatomy to which the device is to be attached.

Attached directly or indirectly to the upper and lower cuffs 22, 25 is a liner arrangement 46, which may take a variety of different forms. In the most preferred embodiments illustrated in the figures, the liner arrangement 46 takes the form of a plurality of discreet segments 49. Each segment 49 preferably comprises a resilient material, which may be formed by moulding for example, cutting or otherwise shaping an appropriate material. Alternatively, in the most preferred embodiments each segment 49 comprises a material such as a soft resilient foam and an outer layer of material which is intended to contact human skin, such as material sold under the trade name DRY-X. This material is preferred for its property of combining a highly durable nylon material with a micro-porous waterproof and breath-able coating, which allows perspiration of the user to escape through the fabric while preventing moisture from entering the brace so as to provide a comfortable feel for the user of the brace 10.

Each segment 49 may also have properties of resilience provided by a fluid, such as air or water, or other substances such as gels. The segments 49 may include a fluid or gel which can be heated or cooled yet is still resilient and conforming, so as to provide an additional therapeutic benefit to the user. Because of their resilience, the segments 49 adapt to the particular leg shape and musculature of the user. This enables the knee brace 10 to accommodate a variety of muscular shapes and sizes, as the resilient segments 49 readily conform to the user's thigh and calf as the cuffs 22, 25 are secured about the user's leg. The brace 10 can be made snug to the user's leg without having to over-tighten the straps 28, 31, 37 and 40. Moreover, the DRY-X material, or other breathable fabric, prevents excess moisture or sweating of the user's leg between the skin and the brace.

The segments 49 may be engaged with upper and lower cuffs 22, 25 by providing those structures with a selected lining, such as a hook and loop fastener arrangement, commonly referred to as "VELCRO®." One half of the VELCRO® material is provided on the rear portion of each segment 49 and can then be engaged with the other half VELCRO® on the upper and lower cuffs 22, 25 so that the segments can be secured in the desired position. This construction has a further advantage that the segments may be repositioned depending upon the requirements of the user. Furthermore, segments of a number of different shapes and sizes having different properties (for example varying properties of resilience or hardness) may be provided and the user may substitute segments or rearrange the location of segments so that a comfortable and effective fit is achieved.

Figure 4B:
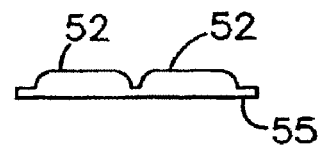
Figure 5A:
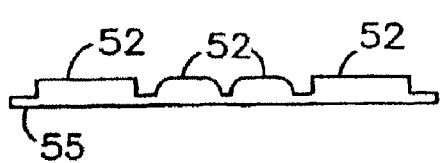
FIG. 5, consisting of FIGS. 5A and 5B, is a plan view and side elevation, respectively, of an alternative embodiment of the liner element.
Figure 5B:
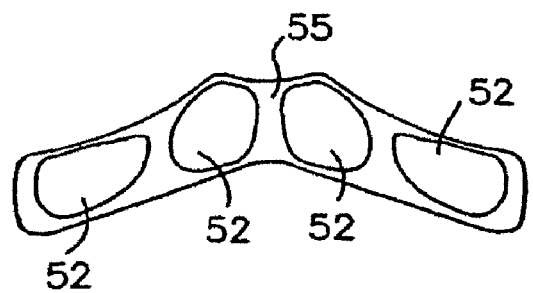

As another alternative, the segments may advantageously be linked together. For example, in FIGS. 4 and 5 segments 52 are illustrated as being interconnected by being placed on a substantially planar substrate 55. As can be seen, each segment 52 protrudes, so that when a rear surface of substrate 55 is affixed to support structure 22, 25 for example, the segments 52 make contact with the body of the user. As discussed above, the segments 52 may also be provided with varying properties, for example varying size (including varying height of protrusion), varying properties of resilience or support, and varying position.

The design of the segments can also be such as to facilitate skeletal grip, quite apart from grip to soft flesh or pure arrangement for user comfort. Therefore, for example the interconnected segments illustrated in FIGS. 4 and 5 may be provided in a knee brace 10 to provide enhanced skeletal grip, for example gripping the tibia.

Figure 6A:
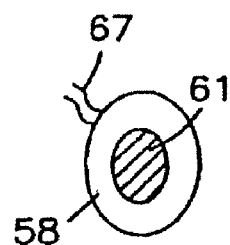
FIG. 6, consisting of FIGS. 6A and 6B, is a front elevation and rear elevation, respectively, of a liner segment having electrophysical modality according to the present invention.
Figure 6B:
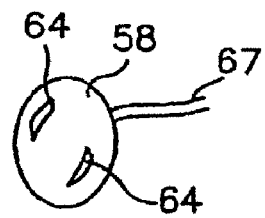
Figure 12:
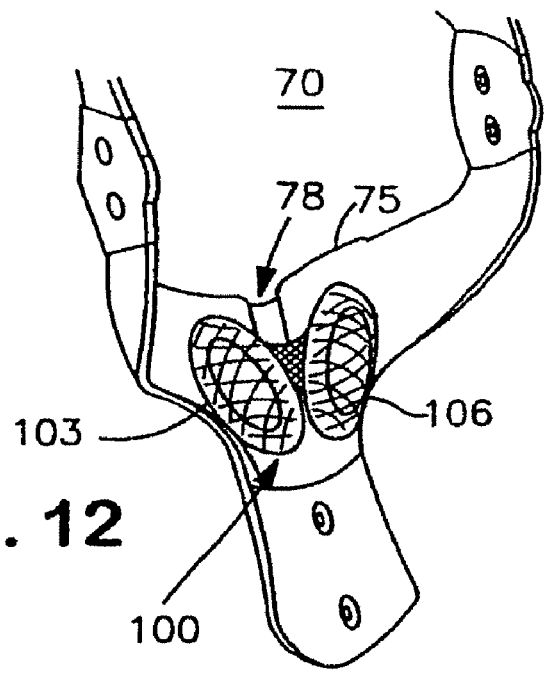
FIG. 12 is a view partially in section of the orthotic device in FIG. 7 and illustrating an alternative embodiment of a segmented tibial liner.

Turning to FIG. 6, yet another application of the invention can be described with reference to segment 58 which on a reverse side can include a VELCRO® attachment 61 to enable the segment 58 to be connected to the support structure 22, 25 of the orthotic device 10, as described above. However, on the side of the segment 58 that contacts the body of the user, the segment includes one or more electrodes 64 which are supplied with electrical energy by one or more conductors

67. The conductors 67 are connected to an electrical source (not shown) such as a portable and lightweight battery pack that can easily be carried on the user's body. By supplying electrical energy in the desired form, the segment 58 can provide Electrophysical Modality such as muscle stimulation, for example stimulating quadriceps muscles in the user's knee, and provide pain relief such as that commonly known as TENS. Each segment (or selected segments) may include one electrode 64, which forms a circuit with another electrode (or electrodes) on other segments 58.

TENS is typically produced through high frequency electrical stimulation of the nerve, which disrupts the pain signal so that the pain is no longer felt. Although the exact mechanism is not yet known, it is believed that TENS works by two different ways. First, electrical stimulation of the nerve fibers can block a pain signal from being carried to the brain. If the signal is blocked, pain is not perceived by the user. Second, the human body has its own mechanism for suppressing pain; it does this by releasing natural chemicals, called endorphins, in the brain which act as analgesics. TENS may activate this mechanism. By using these electrical pulses to stimulate the nerve endings at or near the site of the pain, the user feels diminished pain that is replaced by a tingling or massage-like sensation. The electrical power and circuitry for providing the TENS stimulation can be provided in a small and relatively lightweight package (not shown) which can be worn on the users hip, or directly on the orthotic device, depending on its complexity and size. Thus, the orthotic device 10 of the present invention not only provides the desired support for the user's otherwise weakened knee, but also provides a therapeutic benefit to the user's leg muscles.

One purpose of segmentation is to enhance functionality. Segmentation enables a degree of customization of the interface of the orthotic device with an individual's anatomy so as to achieve better grip and fit. A further function of segmentation provides for better control of components, including electrode components. Each segment of the liner can be viewed as an individual component, and after considering the surface anatomy and characteristics of the tissue interface, customization of a segment provides solutions to variable shape, tissue turgor, soft tissue mobility, and the like. Additional solutions are the incorporation electrodes for physiological modalities, e.g., TENS.

As will be described in more detail hereinafter with respect to FIGS. 7-23, an adjustable liner, or adjustable portions, e.g., segments thereof, can provide multiple solutions to the problem of different anatomy profiles. In general, segments of an adjustable liner can be configured to enhance fit, in effect being customizable for a particular individual. Embodiments of the adjustable liner can include segments thereof which are individually adjustable to suit specific activity levels in individual anatomy to insure optimum control of movement in rotation of portions of the anatomy.

FIGS. 7-23 illustrate certain such embodiments of the invention in the context of a practical example of an application for an adjustable liner according to the invention. Specifically, embodiments of the adjustable liner are illustrated as components of the tibial support member, or cuff, of a knee a brace which interfaces with the anterior border of the tibia (i.e., the shin). The purpose of such a brace is to hold the tibia in position and to prevent it from subluxing (i.e., slipping forward or back or to either side or rotating). To accomplish this purpose, maximum grip is desirable. There is a variety of anatomical shapes in any population group, and frequently a difference between male and female profiles in the anterior tibial border region. The adjustable liner, or adjustable segments thereof, utilized in the tibial region to provide, for example, adjustment for these differences is referred to occasionally hereinafter as an Active Tibial Management (ATM) system.

Although the following drawing figures illustrate, by way of example, such an adjustable liner, or adjustable segments thereof, specifically adapted for positioning in the orthotic device adjacent the tibia of a user; the application for an adjustable liner according to the invention is not limited to use in regard to only the tibia, but can be satisfactorily designed to be used with various other parts of the anatomy, and adjacent not only skeletal structure like the tibia, but also soft tissue. The adjustable liner, and particularly adjustable segment thereof, can be treated as an individual component, which can be individually designed, after considering the surface anatomy and characteristics of the specific tissue interface, to provide solutions to variable shape, tissue turgor, soft tissue mobility, and the like. As mentioned previously, electrodes for physiological modalities can also be incorporated.

Referring now to FIG. 7, an orthotic device 70 is illustrated wherein a lower portion 72 of the orthotic device is adapted to be located adjacent the tibia of a person's leg. Referring to FIG. 8, the lower portion of the device is shown having an ATM back plate 75 including a receptacle, or slot 78, to receive an adjustable tibial liner pad 80 via a rib 81 on the back surface of the adjustable liner 80. As can be seen in FIG. 7, the upper portion 83 of the orthotic device 70 can include an attachment point 85 for other adjustable and/or segmented liners or adaptive element attachments. In addition, upper attachment points 87 for a femoral proximal strap (not shown) and lower attachment points 90 for a gastrochnemius strap (not shown) can also be provided. The adjustable liner 80 can preferably comprise a pair of arm segments, or cams 93, 96, which define a tibial crest alignment groove 99 there between. Each cam segment 93, 96 can be individually adjustable in a variety of ways. In this manner, the cam segments 93, 96 can be manipulated to adjust the shape of the adjustable liner 80.

As shown better in FIGS. 8, 9 and 10, adjustable cams 93, 96 of the tibial liner 80 enable an individual, adjustable fit for specific activity levels and individual anatomy types to ensure optimal movement and rotation of the tibia. The individually adjustable cams 93, 96 enable adjustment on either side of the tibial crest 99 to ensure optimum fit and conformity to an individual's anatomy.

FIG. 9 is a cross section view showing the receptacle, e.g., slot 78, in the ATM back plate 75, and FIG. 10 shows the adjustable tibial liner 80 secured against the ATM receptacle plate 75 with the rib 81 engaged in the slot 78.

Referring now to FIG. 11, the three views illustrate how the adjustable cams 93, 96 are adjustable in a plurality of different ways. As the upper most view shows each cam 93, 96 on opposite sides of the tibial crest 99, can be rotated forwards or backwards to adjust the fit. Additionally, as illustrated in the center view, both of the cams 93, 96 can be adjusted towards each other, or away from each other, to increase or decrease the pressure against the tibia as desired. Finally, the lower view illustrates how the cams 93, 96 can be adjusted to provide increased pressure on only one side of the tibia, to fit an individual's anatomy and to counteract rotation.

Figure 13:
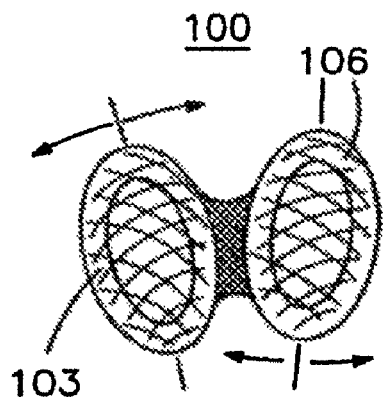
FIG. 13 illustrates an embodiment of a segmented active tibial management liner.
Figure 14:
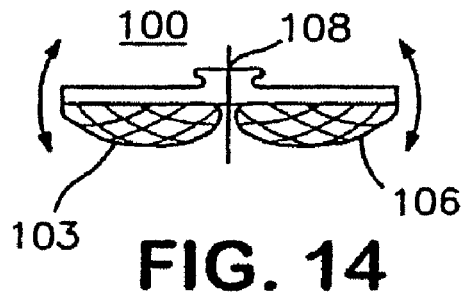
FIG. 14 is a top plan view of the segmental tibial liner element in FIG. 13.

FIGS. 12 through 15 illustrate a further embodiment of an adjustable tibial liner 100, in which the adjustable liner 100 can comprise a pair of pad segments 103, 106 which can be adjusted similarly to the cam segments 93, 96 in the previously described embodiment of the adjustable tibial liner 80. In this present embodiment, the adjustable tibial liner 100 can be secured to the ATM back plate 75 in the same fashion as the adjustable tibial liner 80 described previously, such as via a rib 108 received in the receptacle, i.e., slot 78, in the ATM back plate 75. Each pad segment 103, 106 can be adjusted in the ways illustrated in FIGS. 13-15. As shown in FIG. 13, each pad segment 103, 106 can be individually rotated (clockwise or counter-clockwise), either away from or towards each other. Alternatively, a single pad may be rotated in either such direction without adjustment of the other pad. FIG. 14 shows a second type of adjustment, toward or away from the tibia, which is common with the adjustable arm segments 93, 96 of the adjustable liner 80, as shown in FIG. 11.

Figure 15:
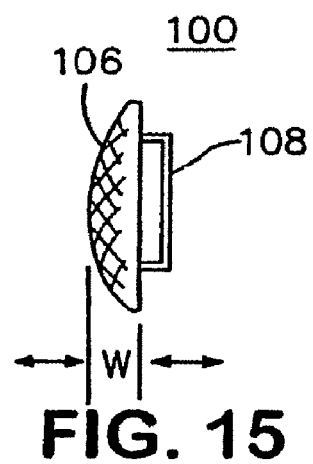
FIG. 15 is a side plan view of the segmented active tibial liner element in FIG. 13.

Referring to FIG. 15, the adjustable tibial liner 100 can additionally be designed such that each pad segment 103, 106 incorporates a pneumatic bladder, to enable each pad segment 103, 106 to expand or shrink. This enables increased control of the individual pressure of each pad segment 103, 106 to counteract tibial rotation, and to also provide a more customized fit relative to the individual's anatomy. As shown in FIG. 15, each pad 103, 106 has a certain thickness, and by provision of a pneumatic system for inflating and/or deflating each individual pad 103, 106, the width "W" of each pad 103,106 can thereby be increased or decreased to control the individual pressure each pad 103, 106 exerts on the tibia.

Figure 17:
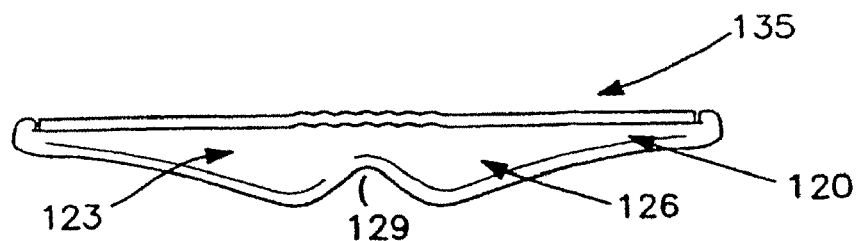
FIG. 17 is a top plan view of the segmented tibial liner in FIG. 16.
Figure 16:
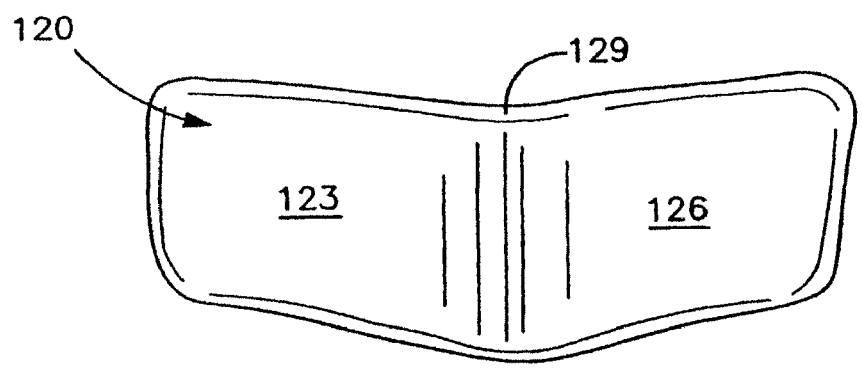
FIG. 16 is a front plan view of a segmented tibial liner.
Figure 18:
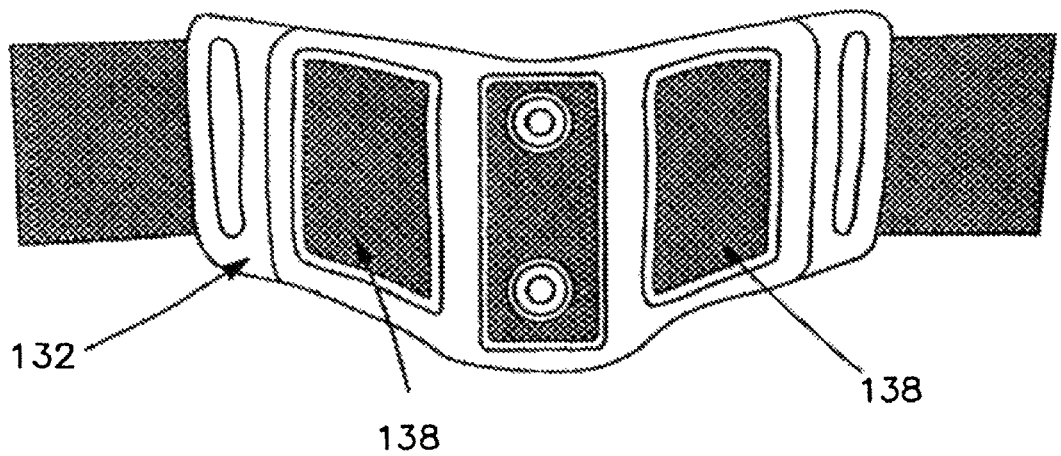
FIG. 18 is a front plan view of a segmented tibial liner receptacle plate, such as on an orthotic device as shown in FIG. 7.

Referring now to FIGS. 16, 17 and 18, a further embodiment of an adjustable tibial liner 120 is illustrated which can be similar to the adjustable tibial liner 80 in FIGS. 7-11. The tibial liner 120 includes cam segments 123, 126 which can be individually adjustable, and which define a tibial crest groove 129 there between. A difference is that the adjustable tibial liner 120 in FIG. 16 is attachable to an ATM back plate 132, such as shown in FIG. 18, via a hook and loop fastener system, e.g., VELCRO®. As shown in FIG. 17, a layer 135 of VELCRO® material can be provided on the back surface of the adjustable liner 120 and can mate with cooperating portions 138 of VELCRO® provided on the ATM plate 132 shown in FIG. 18.

Figure 19:
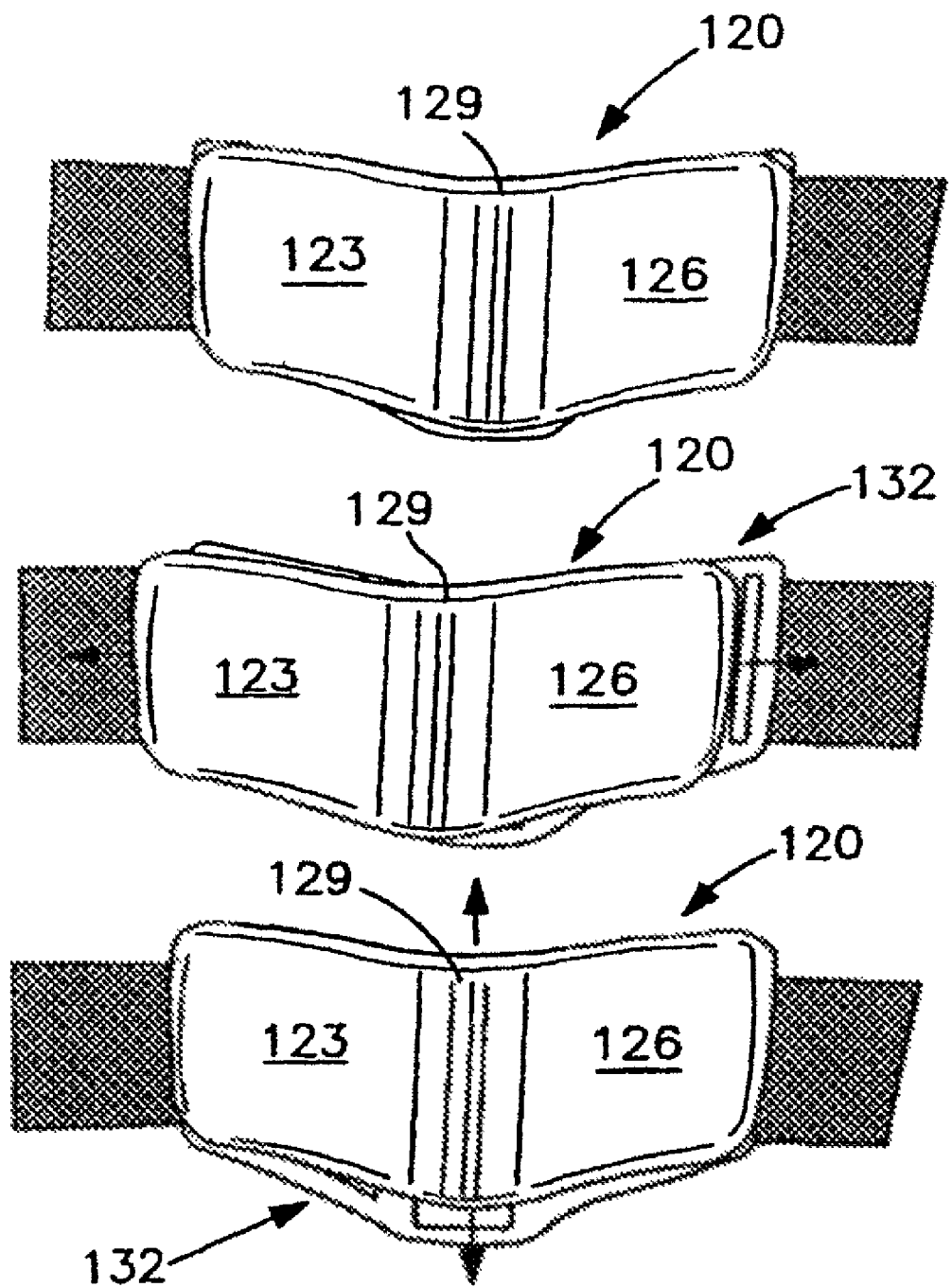
FIG. 19 illustrates variable attachment positions for the segmented tibial liner as shown in FIGS. 16 and 17.

Referring to FIG. 19, the three views show that the adjustable tibial liner 120 can be easily attached at a number of different positions on the ATM plate 132, as enabled by the VELCRO® attachment system. For example, the adjustable liner 120 can be centered on the ATM plate 132 as shown in the top view, or can be offset laterally (left to right) as shown in the center view, or can be offset vertically (up and down) as shown in the bottom view. Additionally, any combination of lateral and vertical offset is also possible.

Referring now to FIGS. 20 and 21, a further embodiment of an adjustable tibial liner 150 is illustrated, wherein the attachment of the liner 150 to the ATM back plate, generally referenced at 162, can be similarly accomplished using a VELCRO® type fastener system as described above. The adjustable tibial liner 150 preferably includes individually adjustable cam segments 153,156 which define a tibial crest groove 159 there between. FIG. 20 is a cross section view of an orthotic device, including the ATM back plate, i.e. at 162, which may be similar to the tibial cuff portion of the orthotic device illustrated in FIG. 18. As with the preceding embodiment, one layer (not shown) of VELCRO® material is affixed to the ATM back plate 162 and a cooperating layer 165 of the VELCRO® material is attached to the mating side of the adjustable tibial liner 150.

Each cam segment 153, 156 can be adjustable in the same manner as the cam segments 83, 86 of the tibial liner 80 illustrated in FIGS. 7-11. Additionally, however, as can be seen in the two lower views of the adjustable tibial liner in FIG. 20, the positioning of the cam segments 153, 156 can further adjusted using chocks 170, i.e., the wedge shaped members illustrated in FIG. 21. The chocks 170 are inserted between the cams 153, 156 and the ATM back plate to further adjust, and maintain, the position of the cam segments 153, 156.

As shown best in FIG. 21, the chocks 170 can be provided in different sizes, and with different angles as shown in the three upper side views of chocks 171, 172 and 173 in FIG. 21. This enables accommodation of varied tibial profiles to customize the fit of the adjustable tibial liner 150, to an individual's anatomy. The chocks 170 can be attached between either or both cams 153. 156 of the tibial liner 150 and the ATM back plate via a VELCRO® type fastener arrangement as described previously. As illustrated, one side of the chock 170 has a layer 175 of VELCRO® material to attach which cooperates with a mating layer 165 of VELCRO®K material on the back of the adjustable tibial liner 150. Additionally, the opposite side of the chock 170 has another layer 178 of VELCRO® material which cooperates with the layer (not shown) of VELCRO® material provided on the ATM back plate.

Referring now to FIGS. 22 and 23, further embodiments of adjustable tibial liners 180 and 190 are illustrated attached to an ATM back plate 188 (shown in cross section). As shown in both FIGS. 22 and 23, the adjustable tibial liners 180 and 190 can be rigidly attached to the ATM back plate 188, for example by a fastener 189, such as a screw or rivet. Each adjustable tibial liner 180, 190 includes individually adjustable cam segments (182, 184 and 192, 194) which define a tibial crest groove (186 and 196) there between.

FIG. 22 illustrates a pair of spacers 187 provided intermediate each cam segment 182, 184 of the adjustable tibial liner 180 and the ATM back plate 188. The spacers 187 can be individually adjusted as to both the position and size thereof to maintain the adjustable tibial liner 180 in a particular position, or configuration, after initial adjustment.

As shown in FIG. 23, pneumatic elements 197 could also be provided instead of, or in combination, with spacers. The pneumatic elements 197 are positioned intermediate each cam segment 192, 194 of the adjustable tibial liner 190 and the ATM back plate 188. The pneumatic elements 197 can be individually inflated, and deflated, to adjust the shape of the liner 190, and/or the positioning of each cam segment 192, 194 to provide individualized fit and activity-specific levels of tibial control, as described previously in regard to other embodiments of the adjustable tibial liner.

Figure 24:
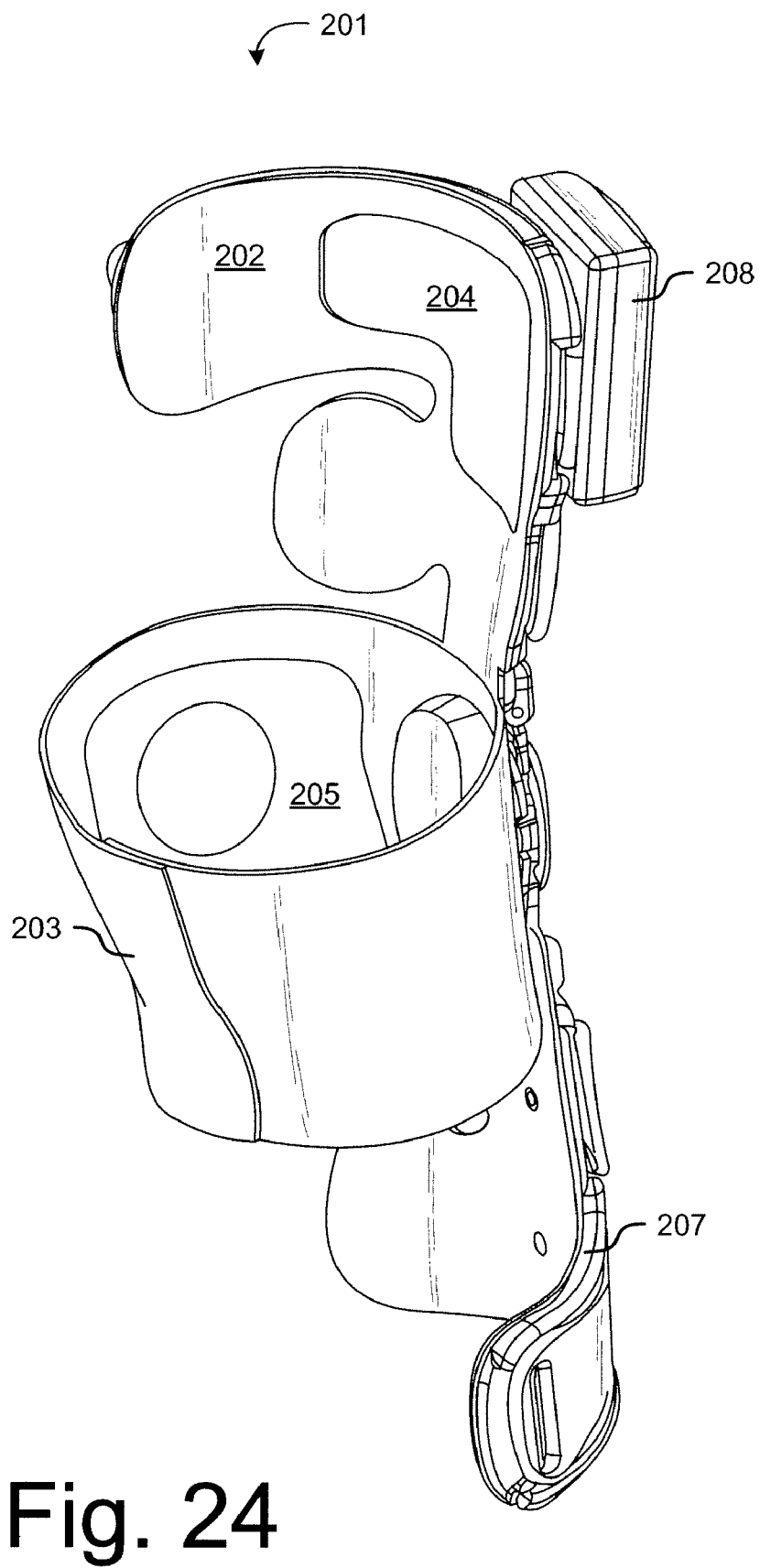
FIG. 24 illustrates a side perspective view of an orthotic device with electrophysical modality components, according to an embodiment of the invention.

FIG. 24 illustrates a side perspective view of an orthotic device with electrophysical modality components, according to an embodiment of the invention. The illustrated orthotic device comprises a knee brace 201 with two electrostimulation pads 204 and 205. Electrostimulation pads 204 and 205 may be used in conjunction with electrostimulation controller 208 to provide electrophysical modalities. Such electrophysical modalities might include, for example Surface Electrical Stimulation (SES), Neuromuscular Electrical Stimulation (NES/NMES), Interferential Stimulation (IS/IF), High Volt Galvanic Stimulation (HVGS), High Volt Pulsed Current (HVPC), Electromagnetic and Pulsed Electromagnetic Field Stimulation (EFS and PEFS/PEMF), Transcutaneous Electrical Nerve Stimulation (TENS), Transcutaneous Electrical Joint Stimulation (TEJS), or Micro Current Electrical Stimulation (MCES). Electrostimulation module 208 is configured to provide the electrostimulation voltages and currents to the leg via the electrostimulation pads.

In various embodiments, the electrostimulation pads may comprise various means to provide electromagnetic fields to a wearer's anatomy. In particular embodiments, electrostimulation pads 204 and 205 comprise resilient or conformable electrodes, such as electrodes composed of conductive fabrics, gels, polymers, liquids, or colloids. Such electrodes allow electrical stimulation to be applied directly to the skin and through the tissue of a wearer while allowing the electrostimulation pads to conform to the wearer's anatomy. For example, a particular electrode might be comprised of an isotopically conducting polymer bladder filled with a conducting fluid configured such that, when the knee brace is worn, the constriction of the knee brace causes the polymer bladder to expand normal to the axis of constriction such that a large conducting surface is formed at the wearer's skin.

Such electrostimulation pads may be coupled to segmented or adjustable liners as described herein. Accordingly, these electrophysical segments may be removable and adjustable in position and angle depending on the wearer's needs and conditions. For example, such electrostimulation pads or segments may be adjustable to improve engagement of the device with the user's anatomy. As another example, in the embodiment illustrated in FIG. 24, a first electrostimulation segment 205 disposed on band 203, which is configured to wrap around a user's knee, and a second electrostimulation segment 204 is disposed on the upper rigid portion within liner 202. In this embodiment, electrostimulation segment 205 may comprise a conductive fabric or flexible conductive polymer such that band 203 is able to conform to the anatomy of a user's knee and electrostimulation segment 204 may comprise a semirigid, resilient element to structurally support the rigid upper portion of the knee brace. For example, electrostimulation segment 204 might comprise a rigid metal conducting element coupled to a conforming conductive pad, such as an electrically conducting gel. The use of SES in this embodiment might comprise transmitting a current from electrostimulation pad 205 to electrostimulation pad 204 such that an electrical signal is transmitted from the knee or lower leg to the thigh.

In other embodiments, further electrostimulation segments might be provided according to the desired electrophysical modality. For example, in a knee brace configured to apply interferential stimulation, a second electrostimulation segment (not shown) may be disposed on the opposite surface of band 203 such that electromagnetic radiation emitted by electrostimulation segment 205 and the second electrostimulation segment constructively interfere at a predetermined location within a user's knee.

In various embodiments, the electrostimulation controller 208 may be configured such that multiple electrophysical modalities may be applied. For example, in the embodiment illustrated in FIG. 24, a third electrostimulation pad may be disposed on the posterior portion of band 203 such that TENS may be applied between electrostimulation segments 204 and 205 during a first time interval and interferential electrostimulation may be applied between electrostimulation segment 205 and the third electrostimulation segment during a second time interval. Other electrodes or electrostimulation pads or segments may be disposed at additional or alternative locations. For example, an electrostimulation segment may be disposed on the lower portion 207, in a substantially similar manner as electrostimulation pad 204.

Figure 25:
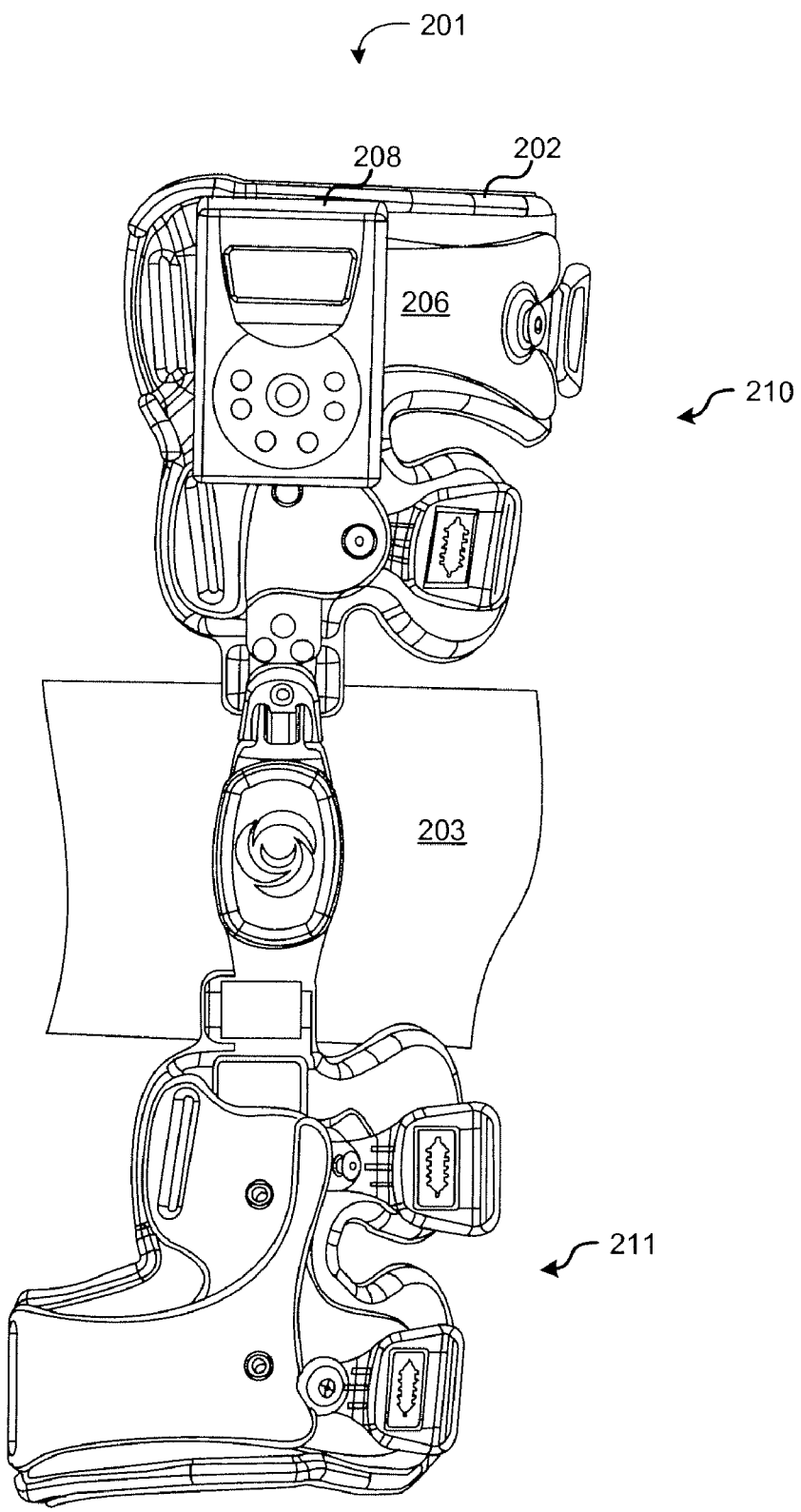
FIG. 25 is a lateral plan view of a knee brace assembly according to an embodiment of the invention.

FIG. 25 is a lateral plan view of a knee brace assembly according to an embodiment of the invention. Knee brace 201 comprises an upper portion 210 configured to engage with and be secured to a wearer's thigh; a band 203 configured to engage with a wearer's knee in a semi-constrictive manner; and a lower portion 211 configured to engage with and be secured to a wearer's calf. Upper portion 210 further comprises an electrostimulation module 208 electrically coupled to a semirigid or soft portion 209. Upper portion 210 may further comprise a liner 202, such as an adjustable or segmented liner as described herein, to allow the brace to conform to a wearer's anatomy in a comfortable manner. As described herein, liner 202 may further comprise electrodes electrically coupled to electrostimulation module 208 to enable electrostimulation module 208 to deliver electrophysical modalities to a wearer.

Knee brace 201 may further comprise a band 203 coupled to the brace such that the brace is maintained in a substantially stable position and such that electrodes may be disposed at a plurality of locations around the anatomy of a user's knee. For example, band 203 may be coupled the hinging portion of knee brace 201 and elastically conform to the circumference of a portion of the user's knee such that the brace is rotationally stable and translationally stable in the distal proximal axis without causing excessive discomfort to a wearer. Accordingly, a surface is provided to adjustably position electrodes on a wearer's knee anatomy and any electrodes positioned on the upper or lower brace portions are maintained in a stable position.

Figure 26:
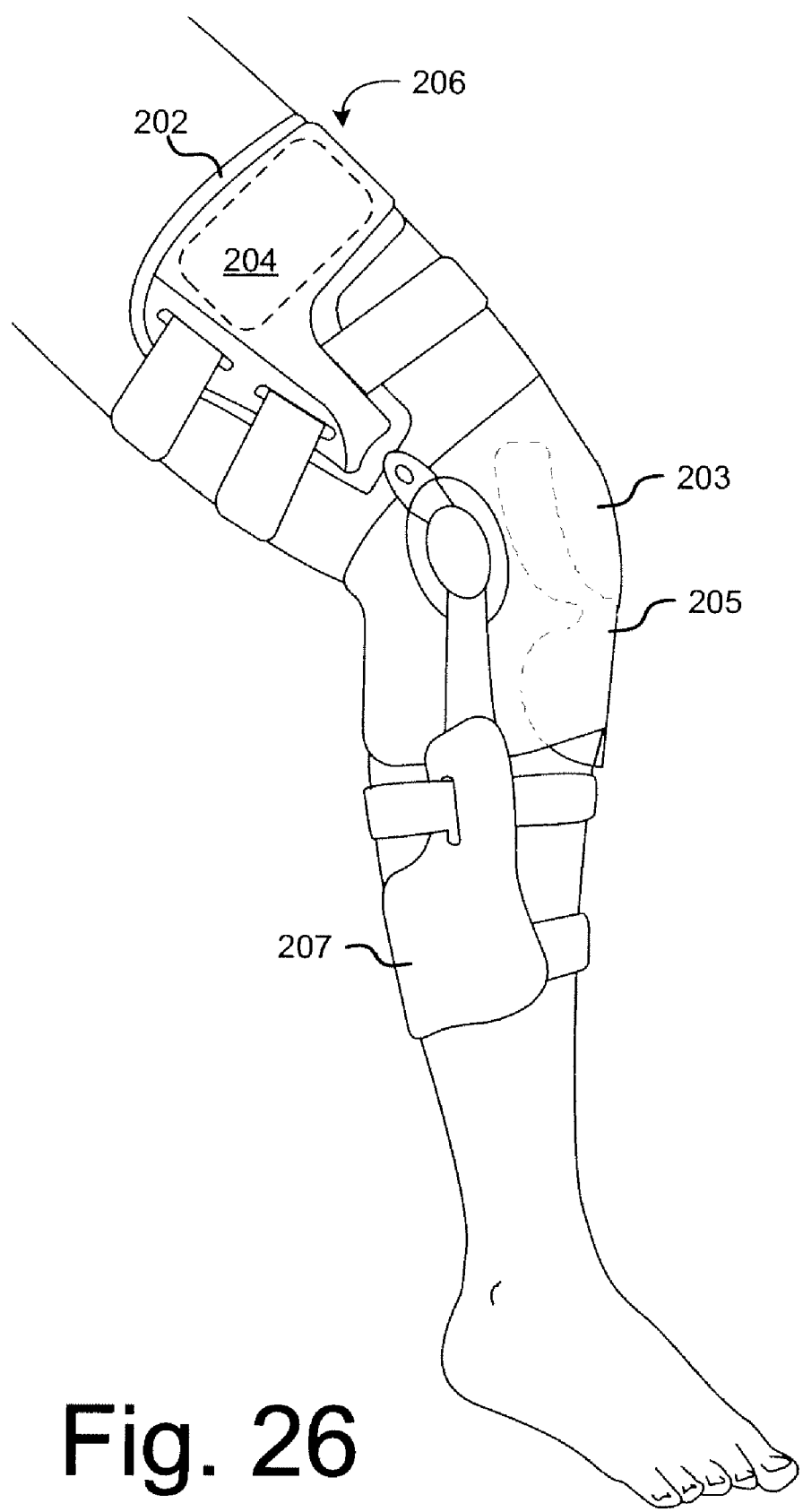
FIG. 26 is a lateral perspective view of a knee brace assembly worn on a user's leg according to an embodiment of the invention.

FIG. 26 is a lateral perspective view of a knee brace assembly worn on a user's leg according to an embodiment of the invention. As illustrated and described herein, the disposition of the upper cuff portion 206 anterior of the wearer's thigh and the disposition of the lower cuff portion 207 posterior to the wearer's calf provide a rigid bracing support system that can impart a relieving force on a user's knee joint. Liner 202 may be an adjustable or segmented liner as described herein to provide a conforming surface with the wearer's anatomy. Band 203 may comprise an elastic or other type of resilient material coupled to the brace hinge or other brace elements to provide positional stability and a surface upon which electrostimulation elements may be disposed. Various electrostimulation modules may be incorporated into such a brace. For example, the illustrated brace comprises an electrostimulation element 204 incorporated into liner 202 and electrostimulation element 205 incorporated into band 203. As described herein, these electrostimulation elements may be configurable or interchangeable according to a wearer-specific and condition-specific electrophysical modality.

Figure 27A:
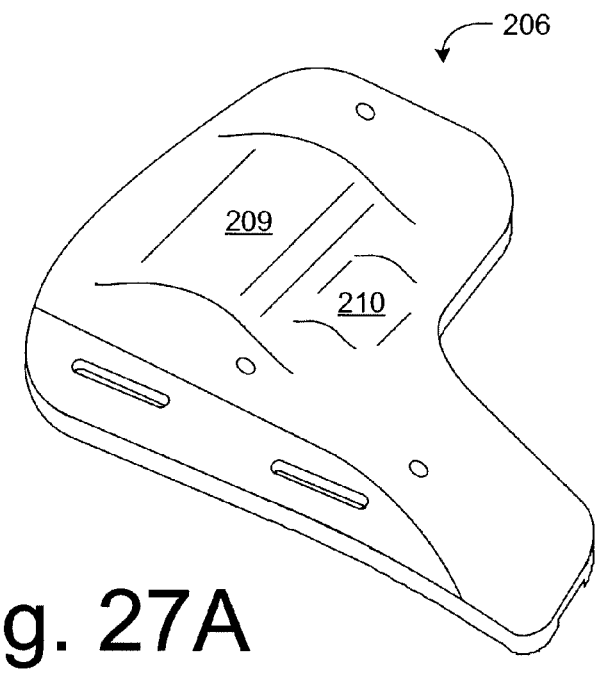
FIGS. 27A and 27B illustrate two examples of thigh cuffs with electrostimulation units according to embodiments of the invention.

FIG. 27 illustrates two examples of thigh cuffs with electrostimulation units according to embodiments of the invention. FIG. 27A illustrates a thigh cuff with an integrated electrostimulation unit according to an embodiment of the invention. The integrated thigh cuff 206 comprises a power source 209, such as a battery, electrically coupled to an electrostimulation unit 210. Electrostimulation unit 210 may comprise a signal generator, such as a programmable signal generator configured to provide a predetermined electrophysical modality. Electrostimulation unit 210 is further coupled to electrodes, such as electrostimulation units 204 and 205 as illustrated in FIG. 26, and is configured to provide an electrical current according to a predetermined electrophysical modality. In some embodiments, such thigh cuffs or stimulation units may be interchangeable according to the electrophysical modality provided. For example, a thigh cuff configured to provide a TEJS treatment may be interchanged with a thigh cuff configured to provide SES treatment if a wearer's condition changes. Or as another example, the electrostimulation unit 210 may be interchangeable within a cuff, such as through a removable panel.

Figure 27B:
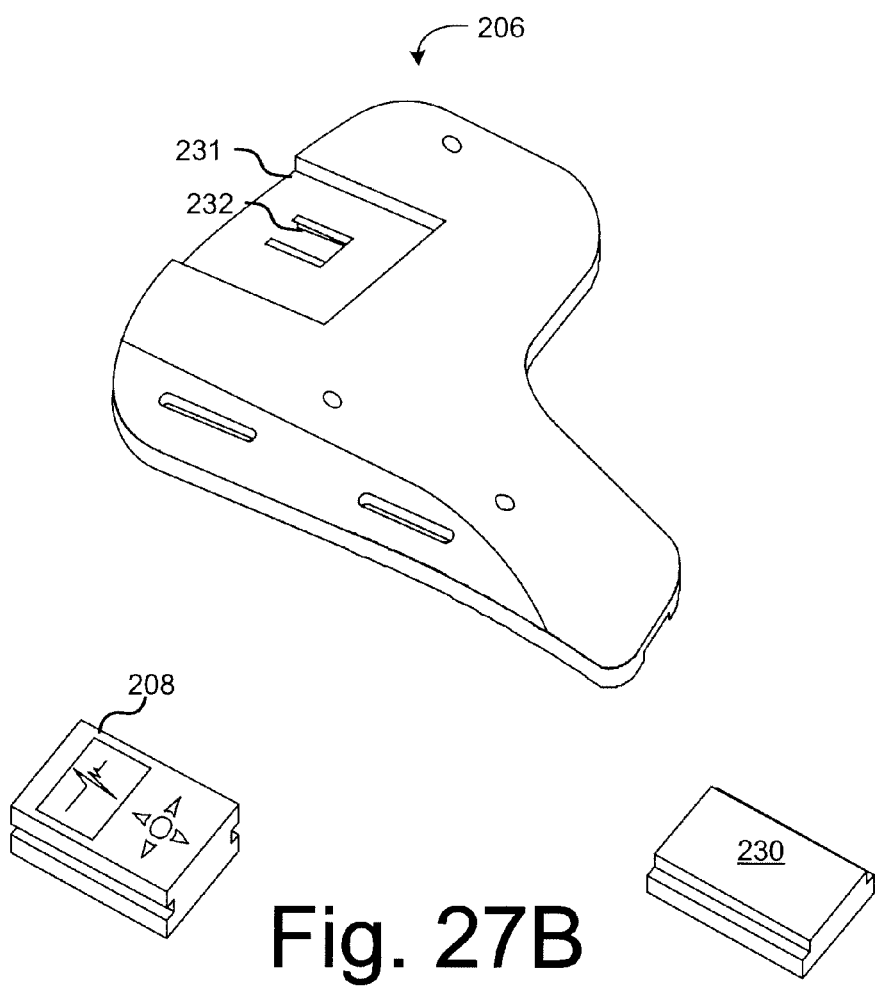

FIG. 27B illustrates a thigh cuff with a detachable signal generator according to an embodiment of the invention. In the illustrated embodiment, thigh cuff 206 comprises a receptacle 231 configured to slidably receive a detachable electrostimulation unit 208. Receptacle 231 may further comprise an electrical contact 232 such that electrostimulation signals generated by electrostimulation 208 are transmitted to electrostimulation pads or electrodes as described herein. Alternatively, feature 232 could also be configured to function as a snap-fit or latch mechanism to lock the electrostimulation unit 208 in place. A faceplate 230 may be provided for insertion into receptacle 231 when electrostimulation unit 208 is not in use or is not prescribed. Such a faceplate 230 may protect electrical contact/latch 232 from the environment and provide a smooth surface contour for thigh cuff 206 when the electrostimulation unit 208 is not in use or is not prescribed.

Figure 28:
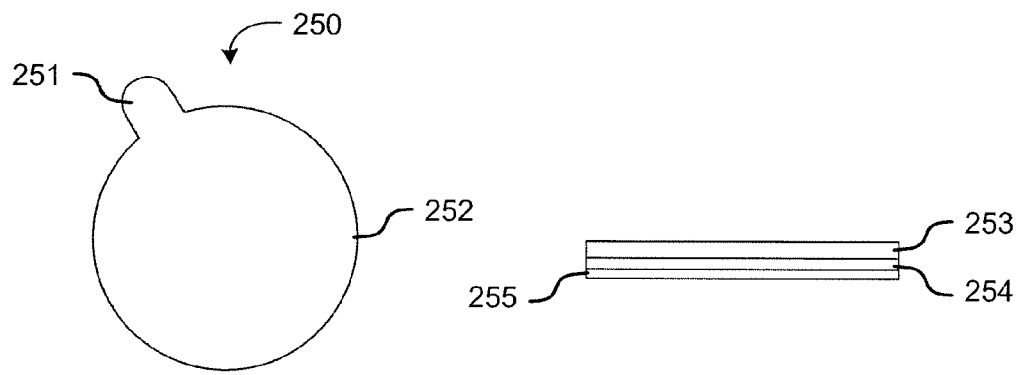
FIG. 28 shows a plan view and a lateral side view of an electrostimulation pad electrode according to an embodiment of the invention.

FIG. 28 shows a plan view and a lateral side view of an electrostimulation pad electrode according to an embodiment of the invention. Electrode 250 has a surface profile comprising an interface portion 252 and a connection portion 251. Interface portion 252 is configured to provide a conductive interface between the electrode and the wearer's anatomy. Interface portion 252 has a profile shaped to serve a particular electrophysical modality. For example, a substantially circular profile may be used to interface with a large muscle group while a thinner or custom shaped profile may be used to interface with a specific joint. Connection portion 251 is configured to allow an electrical connection to be formed between the electrode and an electrostimulation unit.

The embodiment of FIG. 28 comprises three layers: (1) a conductive pad layer 253; (2) a conductive middle layer 254; and (3) a backing layer 255. Conductive pad layer 253 comprises a conductive material to allow electrostimulation signals to be transmitted to a wearer's anatomy and to maintain such transmissions under normal wearing conditions. For example, conductive pad layer 253 may comprise a conductive hydrogel or elastomer that may be elastic, flexible, and conformable such that the electrode maintains contact along the entire interface portion profile 252 during normal body movements.

Conductive middle layer 254 comprises an electrically conductive material to distribute the electrostimulation signals across the interface portion 252 profile. In some embodiments, such as embodiments where the electrode is disposed on a rigid or semirigid portion of an orthotic device, the conductive middle layer 254 may comprise a rigid or semi-rigid conductive material. In other embodiments, such as embodiments where the electrode is disposed on an elastic band or other flexible portion of an orthotic device, the conductive middle layer 254 may comprise a flexible or elastic material. For example, the conductive middle layer 254 may comprise a carbon film or an elastic carbon film that allows the electrode to resiliently deform such that it can conform to a wearer's particular anatomy and maintain conformance during normal motion.

Backing layer 255 provides a surface to attach the electrode to an orthotic device. For example, backing layer 255 might comprise an adhesive, such as a pressure sensitive adhesive, or one side of a VELCRO® adhesive system. In some embodiments, backing layer 255 might comprise an insulating material to ensure proper electrical flow and to avoid inadvertent contact with the conducting layers. In other embodiments, the backing layer may be conductive or may have conductive portions to facilitate electrical connection. For example, the backing layer could comprise one surface of a hook and loop type system composed of conducting hooks and loops while the second surface of the conductive hook and loop system could be disposed on the orthotic device and electrically coupled to the electrostimulation unit. Such a conductive hook and loop system might comprise a hook and loop system composed of a conductive material, or a hook and loop system composed of a non-conductive material coated with a conductive material. In these embodiments, the electrostimulation circuit may be completed merely by attaching the electrostimulation pad to the orthotic device.

Figure 29:
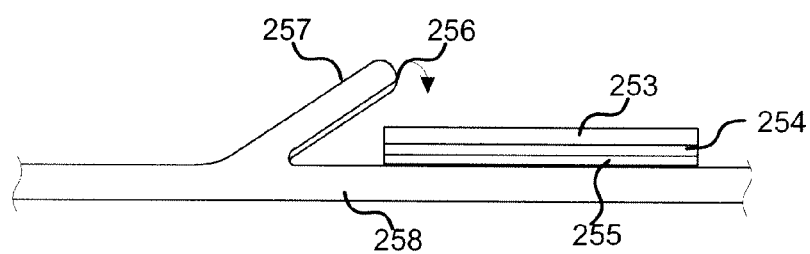
FIG. 29 illustrates a side view of an electrode disposed on an orthotic device according to an embodiment of the invention.

FIG. 29 illustrates a side view of an electrode disposed on an orthotic device according to an embodiment of the invention. The electrostimulation pad 250 is attachable to the orthotic device 258 such that an electrical connection can be formed between the device and the pad. Such an electrical connection may be formed using a connection member 257 comprising a conductive electrical contact 256 embedded in an insulating material. In embodiments where the electrostimulation pad 250 comprises an electrical connection portion 251, connection member 257 may be connectable to connection portion 251. In such embodiments, the connection portion 251 may be recessed in with respect to the interface portion 252, such that the pad has a substantially constant elevation after electrical connection. For example, this may be achieved by reducing or eliminating the conductive pad layer 253 at the connection point, such that the connection member 257 connects directly to the conductive middle layer 254. In other embodiments, this may be achieved by compressive force imparted on the pad by connection member 257 when engaged.

Figure 30:
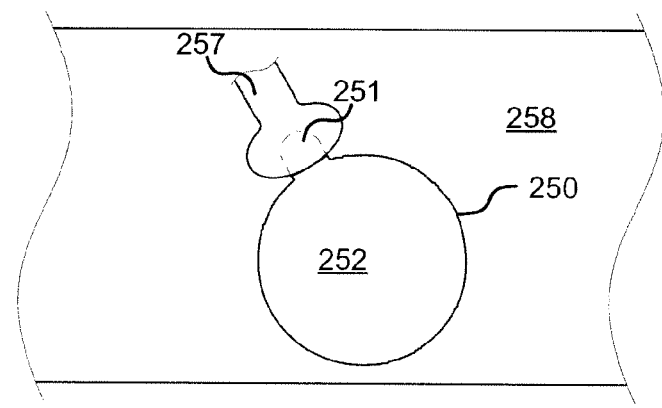
FIG. 30 is a plan view of an electrode disposed on a segmented liner according to an embodiment of the invention.

FIG. 30 is a plan view of an electrode disposed on a segmented liner according to an embodiment of the invention. As illustrated in the plan view, connection member 257 forms an electrical connection with connection portion 251. As described herein, segmented liner 258 may be resilient and adaptable to conform to a wearer's anatomy. Similarly, the electrode 250 and connection member 257 may be resilient and adaptable to also conform to a wearer's anatomy. In the illustrated embodiment, connection member 257 is configured as described with respect to FIG. 29. In other embodiments, connection member 257 may comprise other means of electric connections. For example, electrical connection member 257 may comprise a socket to insertably receive connection portion 251.

Figure 31:
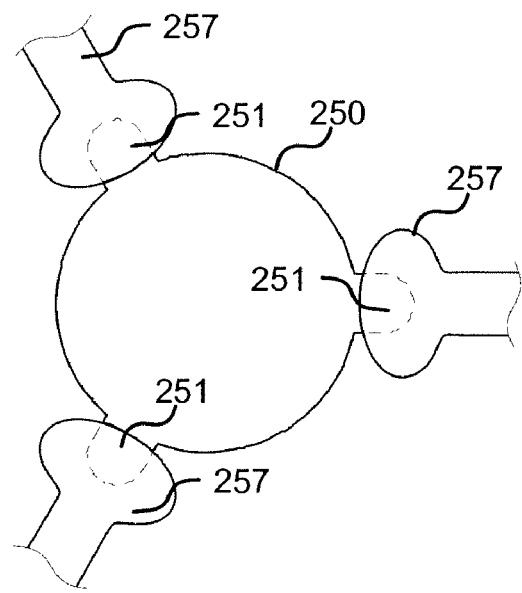
FIG. 31 illustrates an electrode having a plurality of connection portions according to an embodiment of the invention.

FIG. 31 illustrates an electrode having a plurality of connection portions according to an embodiment of the invention. As illustrated, a plurality of connection portions 251 and connection members 257 may be provided for additional stability and to ensure a stable connection. For example, electrode 250 may be disposed on an elastic band, such as an elastic knee band as described herein, and may undergo frequent contorting and stretching forces. Additionally, the use of multiple connection portions 251 and connection members 257 may assist in providing a uniform distribution of electrical energy throughout the electrode. For example, in a large pad, such as when disposed on a thigh, using a single connection member may result in electrical energy bleeding off or concentrating in only a portion of the pad. Accordingly, multiple electrical connection portions 251 may be formed integrally from the electrode layers such that a disruption in the electrical connection at any one portion does not disrupt the transmission of the electrostimulation signals.

Figure 32:
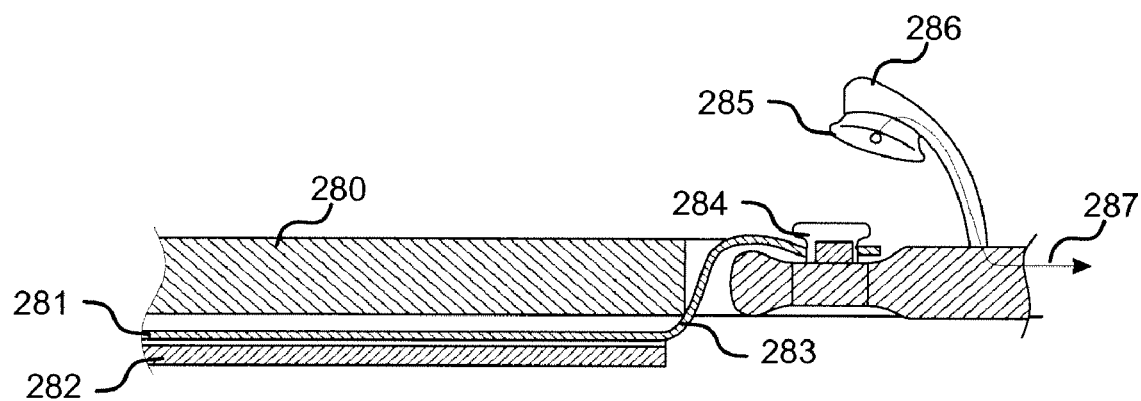
FIG. 32 illustrates a cross-sectional view of an electrode according to an embodiment of the invention.

FIG. 32 illustrates a cross-sectional view of an electrode according to an embodiment of the invention. In some embodiments, these electrodes can be integrated into such segmented liners as described herein. For example, a segmented liner 280 may have a conductive layer 281 and an interface layer 282 disposed thereon. Conductive layer 281 may be formed to have a connection portion 283 to form an electrical connection with an electrostimulation unit through contacts 284 and 285. Electrical contacts 284 and 285 may be configured such that segmented liner 280 may be adjustable and detachable, as described herein. Conductive interface layer 282 may be truncated as shown in FIG. 32, or it may continue uniformly across the entire surface of electrode.

Figure 33:
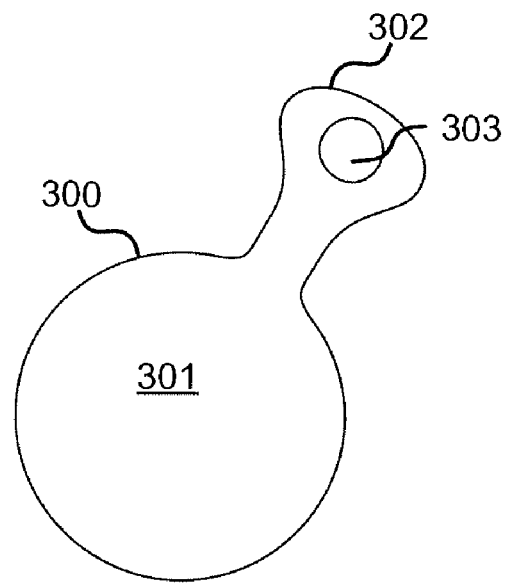
FIG. 33 illustrates a plan view of a further electrode according to an embodiment of the invention.

FIG. 33 illustrates a plan view of a further electrode 300 according to an embodiment of the invention. Electrode 300 may comprise an interface portion 301 and a connection portion 302. The electrode 300 may be formed integrally of three or more layers, as described herein. The outermost interface layer configured to interface with the wearer's anatomy may have a removed space 303, such that the conductive layer is accessible. In such embodiments, electrical connection may be formed with the middle conductive layer without direct connection to the conductive interface layer while avoiding contact between the wearer's anatomy and the conductive middle layer. Accordingly, the electrical charge is distributed evenly throughout the interface portion 301 prior to transmission through the wearer's anatomy.

Figure 34:
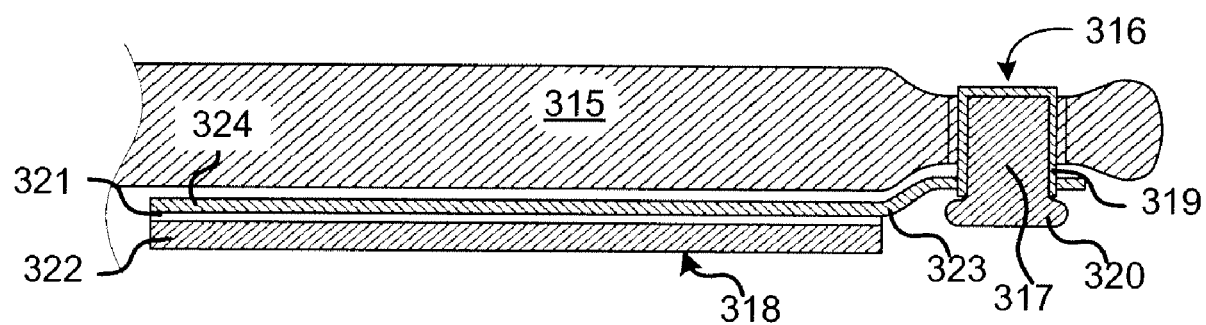
FIG. 34 illustrates a lateral view of an electrode according to an embodiment of the invention.

FIG. 34 illustrates a lateral view of an electrode according to an embodiment of the invention. Segmented liner 315 allows an electrical connection member 317 to interface with electrode 318. For example, connection member 317 may comprise a stem 319 and insulating portion 320 configured such that conductive layers 321 or 322 make electrical contacts through connection portion 323. Stem 319 is conductive, while insulating portion 320 insulates the user from accidental electrical contact with stem 319 if electrode 318 is not installed. In some embodiments, Stem 319 may comprise a conductive coating deposited on insulating portion 320, or a conductive ring attached to insulating portion 320. Attachment methods can include mechanical assembly or inserting ring 319 into insulating portion 317 mold (insert-molding). Stem 319 can include a lead-connection portion 316, for connection to electrostimulation device. For example, connection may occur via soldering, snap, friction/press-fit, or other mechanical means. Electrode 318 may be integrally formed with segmented liner 315, or may be detachable from the liner, for example through a mechanical or adhesive connecting layer 324. For example, a mechanical connecting layer may be a Velcro® hook and loop system. In some embodiments conductive layers 321 or 322 can be truncated as shown, or each (or both) can extend across entire surface of electrode.

Figure 35:
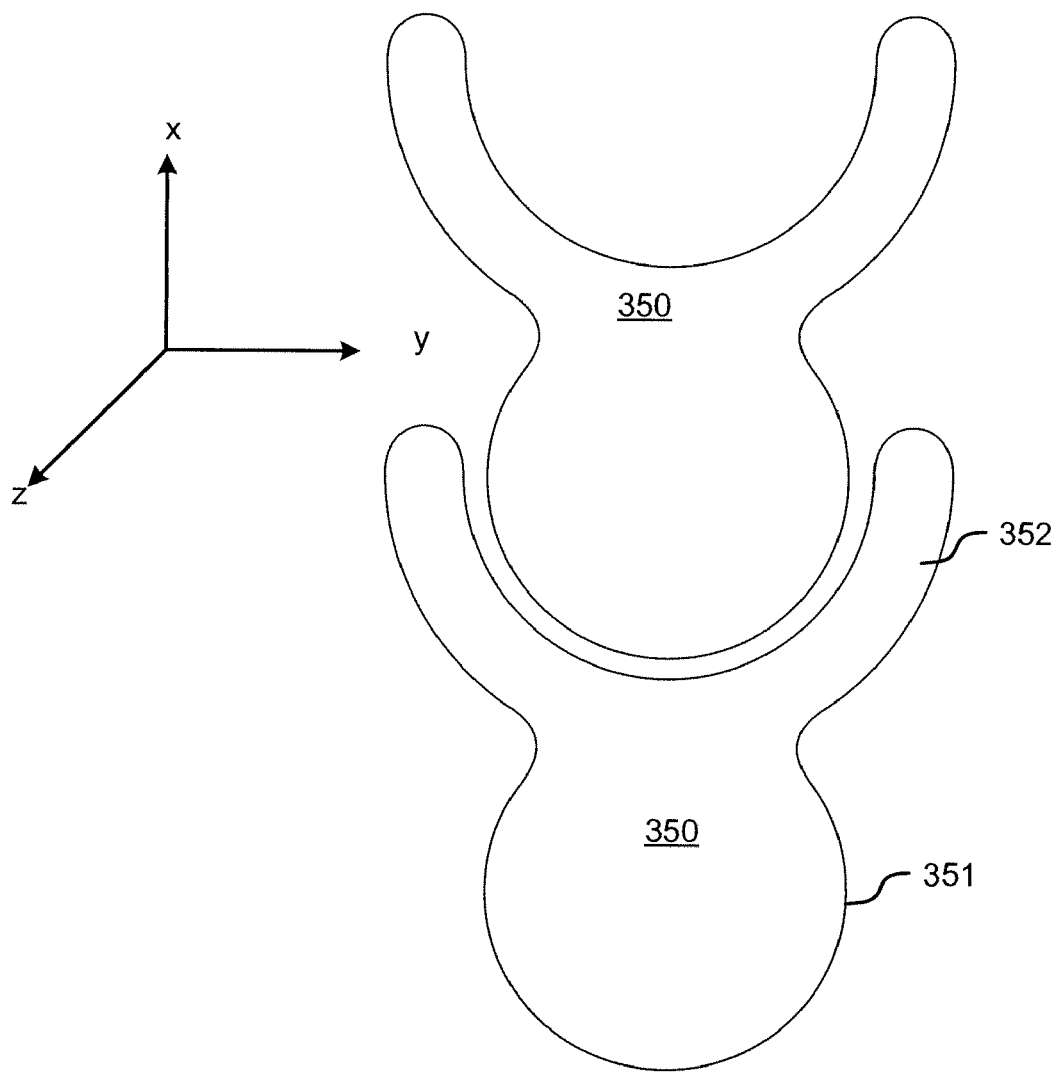
FIG. 35 illustrates a plan view of nesting electrodes according to an embodiment of the invention.

FIG. 35 illustrates a plan view of nesting electrodes according to an embodiment of the invention. Such nesting electrodes may be disposed on orthotic devices that are subject to dynamically changing profiles. The illustrated electrode 351 has a circular interface portion 350 and a crescent or arcuate shaped connecting portion 352. This connection configuration allows for some rotation in the x-y plane, y-z plane, and the x-z plane without folding or breaking the electrical connection between the electrodes. For example, a series of such nested electrodes may be disposed on the inner surface of an elastic orthotic band configured to be disposed around an elbow. Accordingly in this example, the normal movement of a wearer's elbow will not impede the transmission of the electrostimulation signals to the wearer. The nested shape also allows for better material yields with less waste during manufacturing.

Figure 36A:
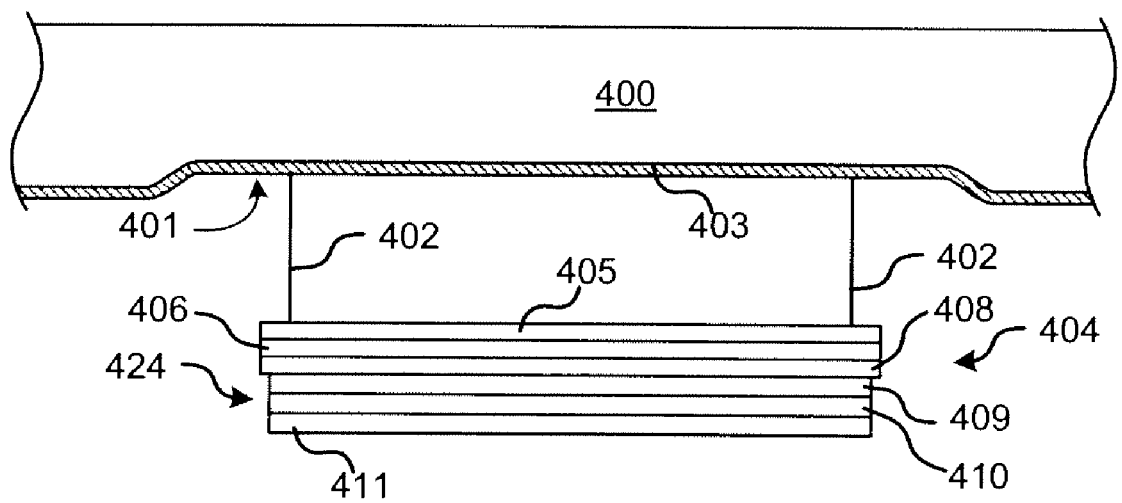
FIGS. 36A-C illustrate lateral views of an adjustable electrode and liner according to an embodiment of the invention.
Figure 36B:
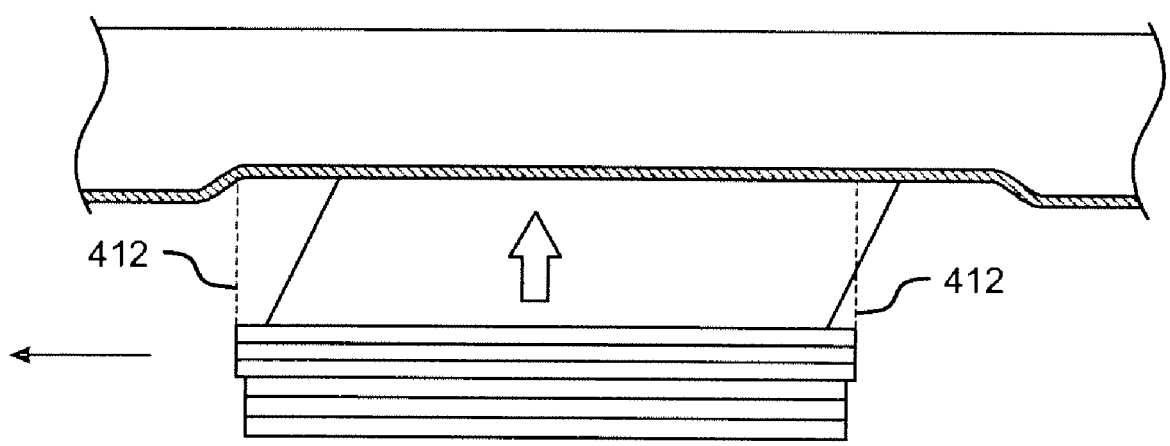
Figure 36C:
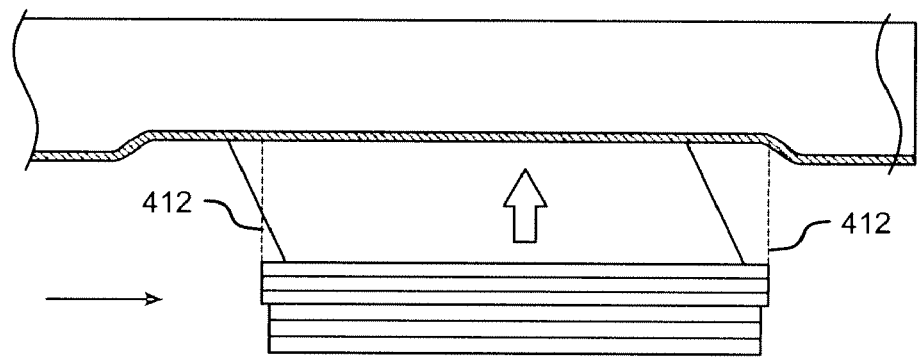

FIGS. 36A-C illustrate lateral views of an adjustable electrode and liner according to an embodiment of the invention. The main liner 400 is disposed on an orthotic cuff, as described herein. For example, main liner 400 may be integrally formed with a brace, or may be attached to a brace, for example through an adhesive. A liner segment 404 is attached to the main liner 400 such that liner segment 404 may be disposed on main liner 400 only within a predetermined range 412. In the illustrated embodiment, tethers 402 provide this attachment. Tethers 402 may comprise one or more structures configured to attach the liner segment 404 to the main liner 400, such as an elastic or an inelastic material.

Main liner 400 further comprises a means to secure the liner segment 404, such as a hook and loop system 403 and 405 disposed on facing surfaces of main liner 400 and liner segment 404. For example, layer 403 may comprise the loop portion and layer 405 may comprise a hook portion, such that a wearer's skin contacts the loop surface rather than the hook surface.

The adjustable electrode and liner further comprises an electrode 424 removably attached to the liner segment 404. As described herein, electrode 424 may comprise an attachment when 408, a backing layer 409, and a conductive interface layer 410. Backing layer 409 may be conductive or have a conductive coating. In some embodiments, the electrical signal can be transmitted by a wire, which is not shown in this Figure. In some embodiments, electrode 424 may be configured to be removed and replaced, for example after a predetermined period of wear or according to a changing electrophysical modality. The main liner 400 may further comprise a recessed area 401 configured to receive the liner segment 404 and electrode 424. The recessed area 401 may define the areas to which the liner segment may be secured. Recessed area 401 may further have a depth configured such that the liner segment 404 and electrode 424 form a matching or substantially matching surface with main liner 400 when worn.

In various embodiments, the electrode or liner segment may have a density or hardness that varies from the remaining brace padding. For example, conductive interface portion 411 may comprise a conductive electrode gel, which may have a lower density than main liner 400. Accordingly, materials of varying densities or hardnesses may be used in construction of the liner segment and electrode such that the three layer system comprising the main liner, liner segment, and electrode has a different resiliency to the one layer system comprising the main liner alone. For example, liner segment 404 may be configured to have a material layer 406 with a different density or hardness as compared to the main liner, to allow proper conformation. In further embodiments, the material densities may be configured according to different desired characteristics. For example, the electrode may make better contact with the wearer if the electrode liner portion is softer than the surrounding main liner.

Figure 37:
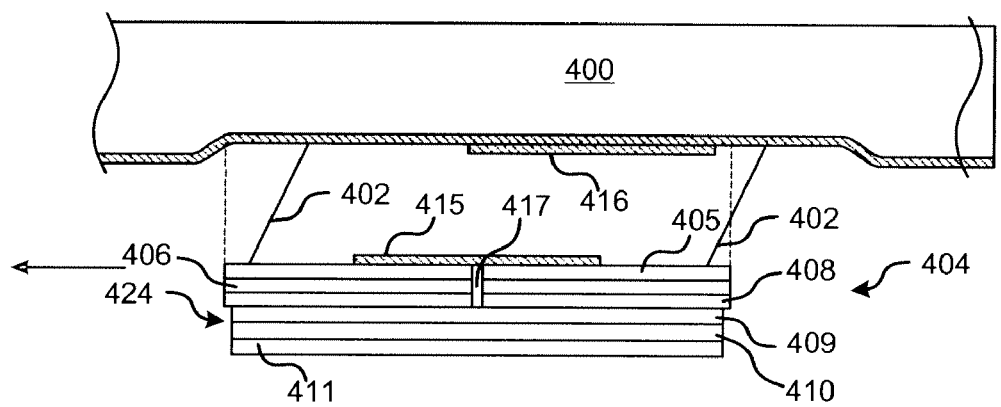
FIG. 37 illustrates a tethered segmented liner and electrode with an electrical contact according to an embodiment of the invention.

FIG. 37 illustrates a tethered segmented liner and electrode with an electrical contact according to an embodiment of the invention. In the illustrated embodiment, features having numbers equivalent to those illustrated with regards to FIGS. 36A-C are equivalent. The embodiment of FIG. 37 further comprises electrical contacts 415 and 416 and electrical connector 417. Electrical contacts 415 and 416 are configured such that when the segmented liner is attached to the main liner 404, electrical contacts 415 and 416 join and electrically couple the segmented liner and electrode to the orthotic device. In some embodiments, electrical contact 416 may be configured such that no matter where within the predetermined range 412 the segmented liner is disposed, no portion of electrical contacts 416 is exposed to a wearer's skin. Electrical connector 417 is electrically coupled to electrical contact 415 and further electrically coupled to electrode 424. Accordingly, when electrode 424 is replaced, as described herein, electrical connection 417 allows the new electrode to be electrically coupled to the orthotic device and electrostimulation unit.

The invention features improvements in relation to skin, skincare and general fit. Since each segment is raised, there are spaces between segments and this allows air to circulate. General fit is improved because the segments allow variations in the contour of the user's body to be accommodated. Furthermore, because the segments effectively provide a noncontiguous surface to the skin of a user, movement of soft tissue, such as muscle, adjacent to one segment is less likely to affect the contact of another segment with the body of the user. Accordingly, a more secure fit is achieved.

Yet another improvement is that the segments tend to keep the support structure, or least edges of the support structure, away from the user's skin. This assists in reducing irritation of the users skin by the relatively more rigid support structure.

While specific embodiments of the invention have been shown in the drawings and described in detail it will be appreciated by those skilled in the art that various modifications and alternatives would be developed in light of the overall teachings of the disclosure. Accordingly, the particular arrangements disclosed herein are meant to be illustrative only and not limiting as to the scope of the invention, which is to be given the full breadth of the appended claims and in any and all equivalents thereof.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to achieve the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A knee brace system, comprising:
   an upper support member adapted to be secured to a thigh;
   a lower support member adapted to be secured to a lower leg;
   a means of connecting the upper support member to the lower support member;
   a conformable, discrete liner segment attached to the upper or lower support member configured to provide an attachment location for a first electrode;
   a first electrode disposed on the liner segment configured to contact the leg;
   a second electrode configured to contact the leg; and
   an electrostimulation unit in electrical contact with the first and second electrodes and configured to provide an electrophysical modality to the leg.

2. The system of claim 1, further comprising a band attached to the connection means and configured to wrap a knee, wherein the second electrode is disposed on the band.

3. The system of claim 2, wherein the first electrode is integral with the conformable, discrete liner.

4. The system of claim 2, wherein the first electrode is removably attached to the conformable, discrete liner.

5. The system of claim 2, wherein the first electrode comprises a conductive gel material.

6. The system of claim 5, wherein the conformable, discrete liner is adjustable and detachable.

7. The system of claim 6, wherein the electrophysical modality is provided to a thigh and knee.

8. The system of claim 1, wherein the upper or lower support member comprises a receptacle to receive the electrostimulation unit.

9. The system of claim 8, wherein the electrostimulation unit is permanently attached to the upper or lower support member.

10. The system of claim 9, wherein the electrostimulation unit is detachable and re-attachable to the upper or lower support member.

11. The system of claim 1, wherein the electrostimulation unit is programmed to provide a plurality of electrophysical modalities and is configured to selectively provide an electrophysical modality of the plurality.

12. The system of claim 1, wherein the liner segment is attached to the upper or lower support member using a tether.

13. The system of claim 1, further comprising a second liner segment attached to the first liner segment using a tether.

14. The system of claim 13, wherein the tether comprises an elastic tether.

15. The system of claim 13, wherein the tether comprises an inelastic tether.

16. An electrostimulation apparatus, comprising:
   an orthotic brace for supporting a portion of an anatomy;
   a support member attached to the orthotic brace;
   a conformable liner attached to the support member;
   an electrostimulation signal generator attached as a part of the support member, the electrostimulation signal generator providing an electrophysical modality to a circuit; and,
   a plurality of electrodes connected to the circuit;
   wherein at least one electrode is disposed on the conformable liner; and, wherein the electrostimulation signal generator is detachable at a location and a cosmetic cover is provided to cover the location when the signal generator is detached.

17. The apparatus of claim 16, wherein the electrostimulation signal generator is configured to be attached to the support member by slidable insertion into a receptacle comprising an electrical contact.

18. The apparatus of claim 16, wherein the support member is further configured to receive a plurality of electrostimulation signal generators configured to provide different electrophysical modalities.

19. The apparatus of claim 16, wherein the electrostimulation signal generator is integrated into the support member.

20. The apparatus of claim 16, wherein the electrostimulation signal generator is programmed to be able to provide a plurality of electrophysical modalities and to selectively provide a modality of the plurality.

21. The apparatus of claim 16, wherein the portion of the anatomy comprises a thigh and knee joint; the discrete liner is disposed on a support member configured to be attached to the thigh; and a second electrode is disposed on a band attached to the orthotic brace and configured to wrap around the knee.

22. The apparatus of 16, wherein the portion of the anatomy comprises a thigh and a lower leg; the discrete liner is disposed on a support member configured to be attached to the thigh; and a second electrode is disposed on a liner disposed on a second support member configured to be attached to the lower leg.

\* \* \* \* \*

UNITED STATES PATENT AND TRADEMARK OFFICE
CERTIFICATE OF CORRECTION

PATENT NO. : 8,070,703 B2  Page 1 of 1
APPLICATION NO. : 12/468794
DATED : December 6, 2011
INVENTOR(S) : Skahan et al.

It is certified that error appears in the above-identified patent and that said Letters Patent is hereby corrected as shown below:

On the Title Page, insert:

-- (63) Related U.S. Application Data
Continuation-in-part of 10/591,966, filed on Sept. 7, 2006, now Pat. No. 7,758,527 which is a 371 of PCT/US05/08010 filed March 10, 2005.

(30) Foreign Application Priority Data
March 10, 2004 (NZ) ......... 531705 --

Signed and Sealed this
Twenty-eighth Day of February, 2012

David J. Kappos
*Director of the United States Patent and Trademark Office*